US012648851B2

(12) United States Patent
De Marchena et al.

(10) Patent No.: US 12,648,851 B2
(45) Date of Patent: *Jun. 9, 2026

(54) TRANSAPICAL REMOVAL DEVICE

(71) Applicant: EVALVE, INC., Santa Clara, CA (US)

(72) Inventors: Eduardo De Marchena, Miami, FL
(US); Chad Abunassar, Alameda, CA
(US); Shengmin Mei, Fremont, CA
(US)

(73) Assignee: Evalve, Inc., Santa Clara, CA (US)

( * ) Notice: Subject to any disclaimer, the term of this
patent is extended or adjusted under 35
U.S.C. 154(b) by 354 days.

This patent is subject to a terminal dis-
claimer.

(21) Appl. No.: 18/448,708

(22) Filed: Aug. 11, 2023

(65) Prior Publication Data

US 2023/0380973 A1 Nov. 30, 2023

Related U.S. Application Data

(63) Continuation-in-part of application No. 16/311,529,
filed as application No. PCT/US2017/038309 on Jun.
20, 2017, now Pat. No. 11,963,712.

(Continued)

(51) Int. Cl.
*A61F 2/24* (2006.01)
*A61B 17/32* (2006.01)
(Continued)

(52) U.S. Cl.
CPC .... *A61F 2/2466* (2013.01); *A61B 17/320016*
(2013.01); *A61B 17/3468* (2013.01);
(Continued)

(58) Field of Classification Search
CPC ................. A61F 2/2466; A61F 2/2454; A61B
17/320016; A61B 17/3468;
(Continued)

(56) References Cited

U.S. PATENT DOCUMENTS 3,378,010 A 4/1968 Codling
3,470,875 A 10/1969 Johnson
(Continued)

FOREIGN PATENT DOCUMENTS

CA 2296317 C 1/2009
DE 9100873 U1 4/1991
(Continued)

OTHER PUBLICATIONS

Dang et al., "Surgical Revision After Percutaneous Mitral Valve
Repair With a Clip: Initial Multicenter Experience," Ann Thorac
Surg 80:2338-2342 (2005).

(Continued)

*Primary Examiner* — Aaron F Roane
(74) *Attorney, Agent, or Firm* — Honigman LLP; Brett A.
Krueger

(57) ABSTRACT

Devices and methods for removing a valve clip which is
pre-positioned on a heart leaflet, the valve clip including a
delivery catheter having a distal end portion configured to be
positioned near a heart valve; a grasping tool deployable
from the distal end portion of the delivery catheter, the
grasping tool configured to grasp and manipulate a valve
clip from an implanted condition to an elongated condition,
wherein the valve clip in the elongated condition has an
elongated width less than an implanted width of the valve
clip in the implanted condition; and a removal tool extend-
able relative to the distal end portion of the delivery catheter,
the removal tool configured to at least partially surround the
valve clip in the elongated condition and to remove the valve
clip from the heart valve leaflet.

25 Claims, 19 Drawing Sheets

Related U.S. Application Data

(60) Provisional application No. 62/352,235, filed on Jun. 20, 2016.

(51) Int. Cl.

| | |
|---|---|
| *A61B 17/34* | (2006.01) |
| *A61B 18/14* | (2006.01) |
| *A61B 18/24* | (2006.01) |
| *A61B 17/00* | (2006.01) |
| *A61B 18/00* | (2006.01) |

(52) U.S. Cl.
CPC .......... *A61B 18/1492* (2013.01); *A61B 18/24* (2013.01); *A61F 2/2454* (2013.01); *A61B 2017/00243* (2013.01); *A61B 2018/00369* (2013.01); *A61B 2018/00577* (2013.01)

(58) Field of Classification Search
CPC ................ A61B 18/1492; A61B 18/24; A61B 2017/00243; A61B 2018/00369; A61B 2018/00577; A61B 17/1285; A61B 17/22; A61B 17/22031; A61B 17/221; A61B 17/32; A61B 17/34; A61B 17/50; A61B 18/02; A61B 18/1445; A61B 2017/00318; A61B 2017/00358; A61B 2017/00876; A61B 2017/22035; A61B 2018/00267; A61B 2018/00273; A61B 2018/0212; A61B 2018/1226
USPC ....................................................... 607/119
See application file for complete search history.

(56) References Cited

U.S. PATENT DOCUMENTS

| | | | |
|---|---|---|---|
| 3,874,388 | A | 4/1975 | King |
| 4,007,743 | A | 2/1977 | Blake |
| 4,055,861 | A | 11/1977 | Carpentier |
| 4,312,337 | A | 1/1982 | Donohue |
| 4,327,736 | A | 5/1982 | Inoue |
| 4,340,091 | A | 7/1982 | Skelton |
| 4,646,719 | A | 3/1987 | Neuman |
| 4,657,024 | A | 4/1987 | Coneys |
| 4,693,248 | A | 9/1987 | Failla |
| 4,716,886 | A | 1/1988 | Schulman |
| 4,795,458 | A | 1/1989 | Regan |
| 4,809,695 | A | 3/1989 | Gwathmey |
| 4,930,674 | A | 6/1990 | Barak |
| 4,998,917 | A | 3/1991 | Gaiser |
| 5,002,562 | A | 3/1991 | Oberlander |
| 5,069,679 | A | 12/1991 | Taheri |
| 5,071,428 | A | 12/1991 | Chin |
| 5,098,440 | A | 3/1992 | Hillstead |
| 5,125,895 | A | 6/1992 | Buchbinder |
| 5,147,370 | A | 9/1992 | McNamara |
| 5,171,259 | A | 12/1992 | Inoue |
| 5,217,460 | A | 6/1993 | Knoepfler |
| 5,222,963 | A | 6/1993 | Brinkerhoff |
| 5,238,002 | A | 8/1993 | Devlin |
| 5,271,544 | A | 12/1993 | Fox |
| 5,327,905 | A | 7/1994 | Avitall |
| 5,330,501 | A | 7/1994 | Tovey |
| 5,334,217 | A | 8/1994 | Das |
| 5,363,861 | A | 11/1994 | Edwards |
| 5,389,077 | A | 2/1995 | Melinyshyn |
| 5,403,326 | A | 4/1995 | Harrison |
| 5,425,744 | A | 6/1995 | Fagan |
| 5,450,860 | A | 9/1995 | O'Connor |
| 5,452,837 | A | 9/1995 | Williamson, IV |
| 5,456,400 | A | 10/1995 | Shichman |
| 5,456,674 | A | 10/1995 | Bos |
| 5,478,353 | A | 12/1995 | Yoon |
| 5,542,949 | A | 8/1996 | Yoon |
| 5,562,678 | A | 10/1996 | Booker |

| | | | |
|---|---|---|---|
| 5,601,224 | A | 2/1997 | Bishop |
| 5,601,574 | A | 2/1997 | Stefanchik |
| 5,607,462 | A | 3/1997 | Imran |
| 5,607,471 | A | 3/1997 | Seguin |
| 5,609,598 | A | 3/1997 | Laufer |
| 5,611,794 | A | 3/1997 | Sauer |
| 5,636,634 | A | 6/1997 | Kordis |
| 5,695,504 | A | 12/1997 | Gifford, III |
| 5,713,911 | A | 2/1998 | Racenet |
| 5,716,417 | A | 2/1998 | Girard |
| 5,741,297 | A | 4/1998 | Simon |
| 5,755,778 | A | 5/1998 | Kleshinski |
| 5,782,239 | A | 7/1998 | Webster, Jr. |
| 5,797,960 | A | 8/1998 | Stevens |
| 5,810,847 | A | 9/1998 | Laufer |
| 5,814,097 | A | 9/1998 | Sterman |
| 5,820,630 | A | 10/1998 | Lind |
| 5,843,178 | A | 12/1998 | Vanney |
| 5,849,019 | A | 12/1998 | Yoon |
| 5,855,601 | A | 1/1999 | Bessler |
| 5,908,420 | A | 6/1999 | Parins |
| 5,976,159 | A | 11/1999 | Bolduc |
| 6,015,417 | A | 1/2000 | Reynolds, Jr. |
| 6,048,351 | A | 4/2000 | Gordon |
| 6,079,414 | A | 6/2000 | Roth |
| 6,117,144 | A | 9/2000 | Nobles |
| 6,120,496 | A | 9/2000 | Whayne |
| 6,139,508 | A | 10/2000 | Simpson |
| 6,149,658 | A | 11/2000 | Gardiner |
| 6,165,183 | A | 12/2000 | Kuehn |
| 6,182,664 | B1 | 2/2001 | Cosgrove |
| 6,193,734 | B1 | 2/2001 | Bolduc |
| 6,200,315 | B1 | 3/2001 | Gaiser |
| 6,217,528 | B1 | 4/2001 | Koblish |
| 6,269,819 | B1 | 8/2001 | Oz |
| 6,290,674 | B1 | 9/2001 | Roue |
| 6,312,447 | B1 | 11/2001 | Grimes |
| 6,332,880 | B1 | 12/2001 | Yang |
| 6,334,860 | B1 | 1/2002 | Dorn |
| 6,346,074 | B1 | 2/2002 | Roth |
| 6,419,640 | B1 | 7/2002 | Taylor |
| 6,419,696 | B1 | 7/2002 | Ortiz |
| 6,461,366 | B1 | 10/2002 | Seguin |
| 6,471,702 | B1 | 10/2002 | Goto |
| 6,482,224 | B1 | 11/2002 | Michler |
| 6,496,420 | B2 | 12/2002 | Manning |
| 6,540,719 | B2 | 4/2003 | Bigus |
| 6,544,215 | B1 | 4/2003 | Bencini |
| 6,551,303 | B1 | 4/2003 | Van Tassel |
| 6,575,971 | B2 | 6/2003 | Hauck |
| 6,599,311 | B1 | 7/2003 | Biggs |
| 6,626,930 | B1 | 9/2003 | Allen |
| 6,629,534 | B1 | 10/2003 | St Goar |
| 6,669,687 | B1 | 12/2003 | Saadat |
| 6,695,866 | B1 | 2/2004 | Kuehn |
| 6,719,767 | B1 | 4/2004 | Kimblad |
| 6,752,813 | B2 | 6/2004 | Goldfarb |
| 6,770,083 | B2 | 8/2004 | Seguin |
| 6,797,002 | B2 | 9/2004 | Spence |
| 6,837,867 | B2 | 1/2005 | Kortelling |
| 6,855,137 | B2 | 2/2005 | Bon |
| 6,875,224 | B2 | 4/2005 | Grimes |
| 6,908,481 | B2 | 6/2005 | Cribier |
| 6,926,730 | B1 | 8/2005 | Nguyen |
| 6,932,810 | B2 | 8/2005 | Ryan |
| 7,011,669 | B2 | 3/2006 | Kimblad |
| 7,101,395 | B2 | 9/2006 | Tremulis |
| 7,112,207 | B2 | 9/2006 | Allen |
| 7,125,421 | B2 | 10/2006 | Tremulis |
| 7,226,467 | B2 | 6/2007 | Lucatero |
| 7,338,467 | B2 | 3/2008 | Lutter |
| 7,556,632 | B2 | 7/2009 | Zadno |
| 7,563,267 | B2 | 7/2009 | Goldfarb |
| 7,569,062 | B1 | 8/2009 | Kuehn |
| 7,604,646 | B2 | 10/2009 | Goldfarb |
| 7,635,329 | B2 | 12/2009 | Goldfarb |
| 7,655,015 | B2 | 2/2010 | Goldfarb |
| 7,666,204 | B2 | 2/2010 | Thornton |
| 7,736,388 | B2 | 6/2010 | Goldfarb |

(56)                References Cited

U.S. PATENT DOCUMENTS

| | | |
|---|---|---|
| 7,811,296 B2 | 10/2010 | Goldfarb |
| 7,972,323 B1 | 7/2011 | Bencini |
| 7,981,139 B2 | 7/2011 | Martin |
| 8,057,493 B2 | 11/2011 | Goldfarb |
| 8,062,313 B2 | 11/2011 | Kimblad |
| 8,118,822 B2 | 2/2012 | Schaller |
| 8,216,230 B2 | 7/2012 | Hauck |
| 8,216,256 B2 | 7/2012 | Raschdorf, Jr. |
| 8,303,608 B2 | 11/2012 | Goldfarb |
| 8,500,761 B2 | 8/2013 | Goldfarb |
| 8,623,077 B2 | 1/2014 | Cohn |
| 8,702,701 B2 | 4/2014 | Suzuki |
| 8,734,505 B2 | 5/2014 | Goldfarb |
| 8,740,920 B2 | 6/2014 | Goldfarb |
| 8,821,518 B2 | 9/2014 | Saliman |
| 8,870,948 B1 | 10/2014 | Erzberger |
| 9,211,119 B2 | 12/2015 | Hendricksen |
| 9,439,757 B2 | 9/2016 | Wallace |
| 9,510,829 B2 | 12/2016 | Goldfarb |
| 9,770,256 B2 | 9/2017 | Cohen |
| 10,076,415 B1 | 9/2018 | Metchik |
| 10,105,222 B1 | 10/2018 | Metchik |
| 10,123,873 B1 | 11/2018 | Metchik |
| 10,130,475 B1 | 11/2018 | Metchik |
| 10,136,993 B1 | 11/2018 | Metchik |
| 10,159,570 B1 | 12/2018 | Metchik |
| 10,231,837 B1 | 3/2019 | Metchik |
| 10,238,493 B1 | 3/2019 | Metchik |
| 10,245,144 B1 | 4/2019 | Metchik |
| 10,258,408 B2 | 4/2019 | Fung |
| D847,983 S | 5/2019 | Ho |
| 10,314,586 B2 | 6/2019 | Greenberg |
| 10,413,408 B2 | 9/2019 | Krone |
| 10,470,881 B2 | 11/2019 | Noe |
| 10,507,109 B2 | 12/2019 | Metchik |
| 10,517,726 B2 | 12/2019 | Chau |
| 10,524,792 B2 | 1/2020 | Hernandez |
| 10,595,997 B2 | 3/2020 | Metchik |
| 10,624,664 B2 | 4/2020 | Cohen |
| 10,631,893 B2 | 4/2020 | Drapeau |
| 10,646,342 B1 | 5/2020 | Marr |
| 10,736,632 B2 | 8/2020 | Khairkhahan |
| 10,751,173 B2 | 8/2020 | Morriss |
| 10,779,837 B2 | 9/2020 | Lee |
| D902,403 S | 11/2020 | Marsot |
| 10,856,988 B2 | 12/2020 | Mcniven |
| 11,602,367 B2 | 3/2023 | Cohen |
| 2002/0013571 A1 | 1/2002 | Goldfarb |
| 2002/0183787 A1 | 12/2002 | Wahr |
| 2003/0069593 A1 | 4/2003 | Tremulis |
| 2003/0167071 A1 | 9/2003 | Martin |
| 2004/0034365 A1 | 2/2004 | Lentz |
| 2004/0044350 A1 | 3/2004 | Martin |
| 2004/0116951 A1 | 6/2004 | Rosengart |
| 2005/0159763 A1 | 7/2005 | Mollenauer |
| 2005/0192633 A1 | 9/2005 | Montpetit |
| 2005/0267493 A1 | 12/2005 | Schreck |
| 2006/0074484 A1 | 4/2006 | Huber |
| 2006/0184198 A1 | 8/2006 | Bales |
| 2007/0038293 A1 | 2/2007 | St Goar |
| 2007/0213735 A1 | 9/2007 | Saadat |
| 2008/0009858 A1 | 1/2008 | Rizvi |
| 2008/0097467 A1 | 4/2008 | Gruber |
| 2008/0140189 A1 | 6/2008 | Nguyen |
| 2009/0012538 A1 | 1/2009 | Saliman |
| 2009/0082857 A1 | 3/2009 | Lashinski |
| 2009/0209955 A1 | 8/2009 | Forster |
| 2009/0209991 A1 | 8/2009 | Hinchliffe |
| 2010/0268226 A1 | 10/2010 | Epp |
| 2011/0009864 A1 | 1/2011 | Bucciaglia |
| 2011/0178366 A1 | 7/2011 | Suzuki |
| 2011/0184405 A1 | 7/2011 | Mueller |
| 2011/0238052 A1 | 9/2011 | Robinson |
| 2012/0022527 A1 | 1/2012 | Woodruff |
| 2013/0197299 A1 | 8/2013 | Chin |

| | | | |
|---|---|---|---|
| 2014/0046320 A1 | 2/2014 | Kappel | |
| 2014/0228871 A1 | 8/2014 | Cohen | |
| 2015/0238729 A1 | 8/2015 | Jenson | |
| 2015/0257883 A1 | 9/2015 | Basude | |
| 2017/0042546 A1 | 2/2017 | Goldfarb | |
| 2017/0049455 A1 | 2/2017 | Seguin | |
| 2017/0100250 A1 | 4/2017 | Marsot | |
| 2017/0239048 A1 | 8/2017 | Goldfarb | |
| 2017/0265994 A1 | 9/2017 | Krone | |
| 2018/0021133 A1 | 1/2018 | Barbarino | |
| 2018/0036119 A1 | 2/2018 | Wei | |
| 2018/0092661 A1 | 4/2018 | Prabhu | |
| 2018/0146964 A1 | 5/2018 | Garcia | |
| 2018/0235657 A1 | 8/2018 | Abunassar | |
| 2018/0242976 A1 | 8/2018 | Kizuka | |
| 2018/0243086 A1 | 8/2018 | Barbarino | |
| 2018/0325671 A1 | 11/2018 | Abunassar | |
| 2018/0344460 A1 | 12/2018 | Wei | |
| 2018/0353181 A1 | 12/2018 | Wei | |
| 2018/0360457 A1 | 12/2018 | Ellis | |
| 2019/0053803 A1 | 2/2019 | Ketai | |
| 2019/0125536 A1 | 5/2019 | Prabhu | |
| 2019/0142589 A1* | 5/2019 | Basude | A61F 2/2463 623/2.11 |
| 2019/0151041 A1 | 5/2019 | Ho | |
| 2019/0151089 A1 | 5/2019 | Wei | |
| 2019/0159899 A1 | 5/2019 | Marsot | |
| 2019/0167197 A1 | 6/2019 | Abunassar | |
| 2019/0183571 A1 | 6/2019 | De Marchena | |
| 2019/0209293 A1 | 7/2019 | Metchik | |
| 2019/0247187 A1 | 8/2019 | Kizuka | |
| 2019/0274831 A1 | 9/2019 | Prabhu | |
| 2019/0321597 A1 | 10/2019 | Van Hoven | |
| 2019/0343630 A1 | 11/2019 | Kizuka | |
| 2019/0350702 A1 | 11/2019 | Hernandez | |
| 2019/0350710 A1 | 11/2019 | Ketai | |
| 2019/0365536 A1 | 12/2019 | Prabhu | |
| 2020/0000473 A1 | 1/2020 | Dell | |
| 2020/0060687 A1 | 2/2020 | Hernández | |
| 2020/0078173 A1 | 3/2020 | Mcniven | |
| 2020/0113678 A1 | 4/2020 | Mccann | |
| 2020/0121460 A1 | 4/2020 | Dale | |
| 2020/0121894 A1 | 4/2020 | Prabhu | |
| 2020/0187942 A1 | 6/2020 | Wei | |
| 2020/0205829 A1 | 7/2020 | Wei | |
| 2020/0214733 A1 | 7/2020 | Drapeau | |
| 2020/0214764 A1 | 7/2020 | Wilder | |
| 2020/0245998 A1 | 8/2020 | Basude | |
| 2020/0261107 A1 | 8/2020 | Cohen | |
| 2020/0281591 A1 | 9/2020 | Krone | |
| 2020/0323528 A1 | 10/2020 | Khairkhahan | |
| 2020/0323549 A1 | 10/2020 | Goldfarb | |
| 2020/0323634 A1 | 10/2020 | Von Oepen | |
| 2020/0360018 A1 | 11/2020 | Dell | |
| 2020/0367871 A1 | 11/2020 | Van Hoven | |
| 2021/0137579 A1 | 5/2021 | Rafiee | |
| 2022/0361907 A1 | 11/2022 | Osterbauer | |

FOREIGN PATENT DOCUMENTS

| | | |
|---|---|---|
| EP | 0558031 B1 | 4/1999 |
| EP | 1383448 A2 | 1/2004 |
| EP | 1383448 B1 | 6/2008 |
| EP | 2760351 B1 | 5/2018 |
| FR | 2705556 A1 | 12/1994 |
| FR | 2768324 A1 | 3/1999 |
| FR | 2768325 B1 | 11/1999 |
| JP | 2016508858 A | 3/2016 |
| WO | 9101689 A1 | 2/1991 |
| WO | 9212690 A1 | 8/1992 |
| WO | 94018893 A1 | 9/1994 |
| WO | 9508292 A1 | 3/1995 |
| WO | 9632882 A1 | 10/1996 |
| WO | 9727807 A1 | 8/1997 |
| WO | 9807375 A1 | 2/1998 |
| WO | 9907295 A1 | 2/1999 |
| WO | 9907354 A2 | 2/1999 |
| WO | 9913777 A1 | 3/1999 |
| WO | 9915223 A1 | 4/1999 |

(56) References Cited

FOREIGN PATENT DOCUMENTS

| | | | |
|---|---|---|---|
| WO | 0003759 | A2 | 1/2000 |
| WO | 0060995 | A2 | 10/2000 |
| WO | 0128432 | A1 | 4/2001 |
| WO | 03020179 | A1 | 3/2003 |
| WO | 03049619 | A2 | 6/2003 |
| WO | 2015057289 | A1 | 4/2015 |
| WO | 2016178722 | A1 | 11/2016 |
| WO | 2018093663 | A1 | 5/2018 |
| WO | 2019058178 | A1 | 3/2019 |
| WO | 2021007324 | A1 | 1/2021 |
| WO | 2021113785 | A1 | 6/2021 |

OTHER PUBLICATIONS

European Search Report dated Oct. 10, 2022 in Application No. EP 22173362, 8 pages.
Extended European Search Report dated May 19, 2021 in Application No. EP 18859611. 7 pages.
European Search Report dated May 4, 2021 in Application No. EP 21161291. 6 pages.
International Search Report and Written Opinion for Application No. PCT/US2017/038309, dated Aug. 21, 2017. 8 pages.
International Search Report and Written Opinion mailed Jan. 8, 2019 in International Application No. PCT/IB2018/001188, 17 pages.
International Search Report mailed Mar. 11, 2013 in International Application No. PCT/US2012/058139, 19 pages.
Rose et al., "Late MitraClip Failure: Removal Technique for Leaflet-Sparing Mitral Valve Repair," Journal of Cardiac Surgery 27:543-545 (2012).

* cited by examiner

FIG. 13

XTW @ 30° (11.4mm)

TRANSAPICAL REMOVAL DEVICE

CROSS-REFERENCE TO RELATED APPLICATION

This is a continuation-in-part application of U.S. patent application Ser. No. 16/311,529, filed Dec. 19, 2018, which is a U.S. national stage of International Application No. PCT/US17/38309, filed Jun. 20, 2017, which claims the priority of U.S. Provisional Patent Application No. 62/352,235, filed Jun. 20, 2016, and entitled "Transapical Removal Device"; the entire contents thereof are incorporated by reference herein.

FIELD OF THE DISCLOSURE

This disclosure relates generally to a transapical removal device, and more specifically, to a transapical removal device for removal of a valve clip, such as a mitral valve clip, or the anterior leaflet of the mitral valve.

BACKGROUND

Mitral valve regurgitation occurs when a heart's mitral valve does not close tightly, allowing some blood to leak backward through the mitral valve into the atrium rather than flowing through the aortic valve. Mitral valve regurgitation is present in approximately 1.7% of the adult population, and the incidence rises with advancing age such that more than 9% of adults 75 years of age and older have moderate or severe mitral valve regurgitation. Because blood cannot move through the heart or to the rest of the body as efficiently in people suffering from mitral valve regurgitation, symptoms include shortness of breath and fatigue, as well as heart murmur, heart palpitations, and swollen feet or ankles. Severe valve regurgitation can lead to heart failure, atrial fibrillation, and pulmonary hypertension. If left untreated, the one year mortality rate for mitral valve regurgitation is 57%.

A variety of treatment options have been developed to treat mitral valve regurgitation, including medications, open-heart surgery, and minimally-invasive procedures. One treatment option involves clipping together mitral valve leaflets of the mitral valve using a valve clip in order to improve the function of the mitral valve. Under certain circumstances removal of a previously installed valve clip can be necessary. For example, mitral valve regurgitation can re-occur after installation of a valve clip, and removal of the valve clip can be desired to facilitate further treatment, such as installation of a mitral valve replacement device. A previously installed valve clip can be removed surgically. However, such procedures can cause elevated morbidity and mortality. Accordingly, there remains a need for minimally invasive systems and methods for removing a previously-installed valve clip. Additionally, some known valve clips have larger device profiles when clipped to mitral valve leaflets, which can make removal of the valve clip more difficult. For example, minimally invasive removal of a valve clip having a larger device profile can require a removal catheter system having a larger diameter, which can lead to an increased risk of bleeding and/or healing issues. Accordingly, there remains a need for minimally invasive systems and methods for removing a previously installed valve clip having a larger device profile.

SUMMARY OF THE DISCLOSURE

The current disclosure is directed to multiple arrangements of a transapical removal device that can be deployed in a catheter procedure to capture for removal or alteration a valve clip or heart tissue, such as the anterior leaflet of the mitral valve, as well as to methods of use of such a transapical removal device. The removal device can include a delivery catheter having a distal end portion configured to be positioned near a heart valve. The removal device can also include a grasping tool deployable from the distal end portion of the delivery catheter, which is configured to grasp and manipulate a valve clip from an implanted condition to an elongated condition such that the valve clip in the elongated condition has an elongated width which is less than an implanted width of the valve clip in the implanted condition. The removal device can also include a removal tool which is extendable relative to the distal end portion of the delivery catheter, and which is configured to at least partially surround the valve clip in the elongated condition and to remove the valve clip from the heart valve leaflet.

The grasping tool can include a hook. Additionally or alternatively, the grasping tool can be configured to be moved between an open state and a closed state. Additionally or alternatively, the grasping tool can include opposing hooks coupled to move between the open state, wherein the distal ends of the opposing hooks are spaced apart, and the closed state, wherein the distal ends of the opposing hooks adjacent each other. Additionally or alternatively, the opposing hooks can be biased toward the open state when they are deployed from the distal end portion of the delivery catheter, and urged toward the closed state when they are retracted relative the distal end portion of the delivery catheter. Additionally or alternatively, the grasping tool can include a snare defining a loop opening which is configured to be moved from the open state, in which the loop opening defines a first diameter, toward the closed state, in which the loop opening defines a smaller second diameter to grasp the valve clip. Additionally or alternatively, the grasping tool can include an alignment wire configured to be positioned within the loop opening of the snare to align the snare relative to the valve clip.

The removal tool can include a sheath, and the sheath can define a sheath lumen, which can at least partially surround the valve clip when the sheath is in the elongated condition. Additionally or alternatively, the delivery catheter can be at least partially disposed within the sheath lumen. Additionally or alternatively, the removal tool can include a cutting blade at the distal end of the sheath which can be used to remove the valve clip from the heart valve leaflet. Additionally or alternatively, the removal tool can include an ablation device coupled to the sheath to remove the valve clip from the heart valve leaflet. The ablation device can include at least one electrode to supply radiofrequency energy to ablate the heart valve leaflet and/or an optical fiber to deliver a laser ablation signal to ablate the heart valve leaflet. Additionally or alternatively, the removal device can include an ablation source in communication with the ablation device, wherein the ablation source is one of a radiofrequency source, laser source, and cryo-thermal source.

The delivery catheter can include an elongate shaft and a handle including a drive mechanism configured to move the distal end portion of the delivery catheter relative to the handle. Additionally or alternatively, the drive mechanism can include threading and a rotatable knob, at least one push-pull lever, and/or at least one plunger.

The removal device can further include a stabilizing tool configured to hold the valve clip. The grasping tool can be configured to grasp a first portion of the valve clip and the stabilizing tool can be configured to hold a second portion of the valve clip. Additionally or alternatively, the grasping tool can be configured to apply a first force to the first portion of the valve clip and the stabilizing tool can be configured to apply a second force to the second portion of the valve clip, wherein the second force is opposite the first force. Additionally or alternatively, the stabilizing tool can include a pair of opposing arms which can be moveable between an open condition and a closed condition.

The current disclosure further includes methods for removing a valve clip pre-positioned on a heart valve leaflet. Methods in accordance with the disclosed subject matter include delivering, to a chamber of a heart, a removal device, the removal device including a delivery catheter having a distal end portion configured to be positioned near a heart valve, a grasping tool deployable from the distal end portion of the delivery catheter, the grasping tool configured to grasp and manipulate a valve clip pre-positioned on a heart valve leaflet, and a removal tool extendable relative to the distal end portion of the delivery catheter, the removal tool configured to at least partially surround the valve clip and to remove the valve clip from the heart valve leaflet. Methods for removing a valve clip pre-positioned on a heart valve leaflet further include deploying the grasping tool to grasp a first portion of the valve clip, manipulating the valve clip from an implanted condition to an elongated condition, wherein the valve clip in the elongated condition has an elongated width less than an implanted width of the valve clip in the implanted condition, at least partially surrounding the valve clip in the elongated condition with the removal tool, and removing the valve clip from the heart valve leaflet using the removal tool.

BRIEF DESCRIPTION OF THE DRAWINGS

FIG. 13 is an example block diagram 100 illustrating the various components used in implementing an example arrangement of a method of using a transapical removal device 102.

DETAILED DESCRIPTION

Figures 1A, 1B:
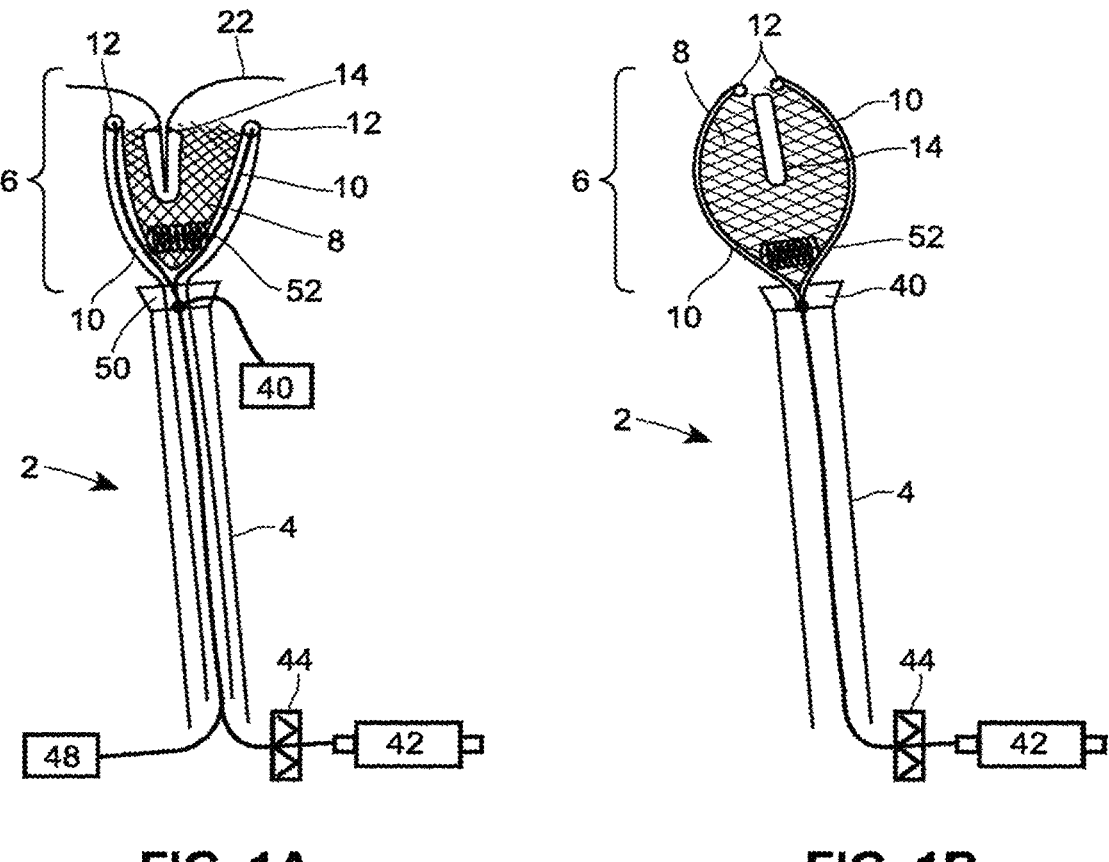
FIG. 1A illustrates a top view of a first arrangement of a transapical removal device of the present disclosure with the snare head in a deployed state.
FIG. 1B illustrates a top view of the first arrangement of the transapical removal device of FIG. 1A with the snare head in a collapsed state.

FIGS. 1A and 1B illustrate a first arrangement of a transapical removal device 2 of the present disclosure. The transapical removal device 2 includes a delivery catheter 4, a snare head 6, a snare basket 8, a spring 52, and ablation delivery catheters 10 with electrodes 12. An electrical source 42 and an ablation source 48 are in communication with the electrodes 12, and a switch 44 alternately permits and ceases to permit electrical current from the electrical source 42 to flow to the electrodes 12. In FIG. 1A, the snare head 6 and snare basket 8 are in a deployed state outside of the delivery catheter 4, and a mitral clip 14 is surrounded by the sides of the snare basket 8. The electrodes 12 of the ablation delivery catheters 10 are aligned with tissue of the heart that is to be ablated in order for the mitral clip 14 to be captured. For example, such tissue may be ablated when a control signal is provide to activate the ablation source 48 to provide an ablation signal, such as a radiofrequency signal, through the catheter 10 to ablate tissue of the mitral valve. FIG. 1B depicts the transapical removal device 2 after ablation has occurred and the mitral clip 14 has been captured by the snare basket 8. The snare head 6 is now in a collapsed configuration and can be removed from the heart, e.g., by being retracted through the delivery catheter 4. The transition of the snare head 6 between the collapsed state and the deployed sate is controlled by a snare head controller 40 connected at a proximal end of the delivery catheter 4. A retraction funnel 40 is provided to forcibly return the snare head to a collapsed state. The spring 52 is compressed when the snare head 6 is in the collapsed state and at rest when the snare head 6 is in the deployed state. For this catheter-based removal technique, the snare head 6 may apply pressure to the captured mitral valve clip 14 to collapse the clip down to a size or close to that of its initial size prior to deployment. This will allow the clip 14 to be removed through the catheter 4 more easily. It is noted that in some instances a slightly larger diameter delivery catheter 4 may be desired (in comparison to the original mitral valve clip delivery catheter) to compensate for tissue attached to the mitral valve clip 14 and ablated by the delivery catheters 10.

Figures 2A, 2B, 2C, 3A, 3B, 3C:
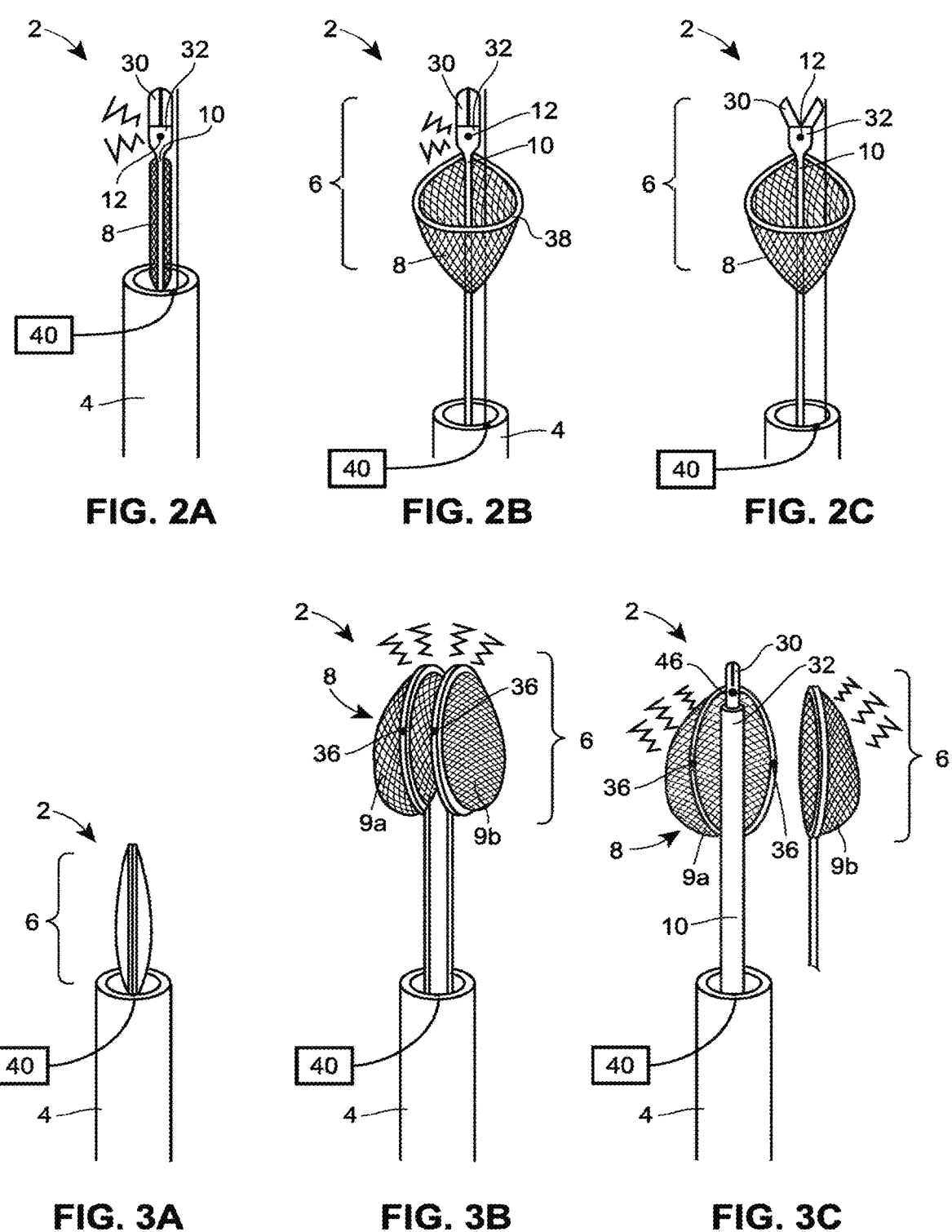
FIG. 2A illustrates an isometric side view of a second arrangement of a transapical removal device of the present disclosure with the snare head in a collapsed state wand a grasping tool of the snare head in a closed state.
FIG. 2B illustrates an isometric side view of the second arrangement of the transapical removal device of FIG. 2A with the snare head in a deployed state and the grasping tool of the snare head in a closed state.
FIG. 2C illustrates an isometric side view of the second arrangement of the transapical removal device of FIGS. 2A and 2B with the snare head in a deployed state and the grasping tool of the snare head in an open state.
FIG. 3A illustrates an isometric side view of a third arrangement of a transapical removal device of the present disclosure with a snare head in a collapsed state.
FIG. 3B illustrates an isometric side view of the third arrangement of the transapical removal device of FIG. 3A with the snare head in a deployed state and the snare basket of the snare head in a closed state.
FIG. 3C illustrates an isometric side view of the third arrangement of the transapical removal device of FIGS. 3A and 3B with the snare head in a deployed state, the snare basket of the snare head in an open state, and a retractable grasping tool of the snare head in a closed state.

FIGS. 2A-2C illustrate a second arrangement of a transapical removal device 2 of the present disclosure. In addition to the elements discussed with respect to FIGS. 1A and 1B, the second arrangement of the transapical removal device 2 includes a grasping tool 30 controllable by the snare head controller 40. The grasping tool 30 is movable between a closed state (shown in FIGS. 2A and 2B) and an open state (shown in FIG. 2C) and is configured to allow manipulation of tissue or the mitral valve clip as needed. The grasping tool 30 may be retractable such that it is controllably movable between a position inside a tube 32 and a position outside the tube 32. The snare basket 8 of the transapical removal device 2 depicted in FIGS. 2A-2C is closed by pulling on a cord 38, optionally using the grasping tool 30, in order to cinch the snare basket 8 closed.

FIGS. 3A-3C illustrate a third arrangement of a transapical removal device 2 of the present disclosure. The third arrangement of the transapical removal device 2 includes the elements disclosed with respect to the first and second arrangements. In the third arrangement of the transapical removal device 2, the snare head 6 has a two-part snare basket 8 having a first basket side 9a and a second basket side 9b. The third arrangement of the transapical removal device 2 allows the transapical removal device 2 to move between a collapsed state (shown in FIG. 3A), a deployed and closed state in which the first basket side 9a and the second basket side 9b are arranged to secure a mitral valve clip, tissue, or another element between them (shown in FIG. 3B), and a deployed and open state in which the first basket side 9a and the second basket side 9b are separated from one another, such as by being rotated to be at an angle relative to each other (shown in FIG. 3C). The first basket side 9a and the second basket side 9b have magnets 36 disposed on them that attract one another and thus facilitate moving the snare basket 8 to a closed state. In the third arrangement, ablation of heart tissue is achieved by an optical fiber 46.

Figure 4:
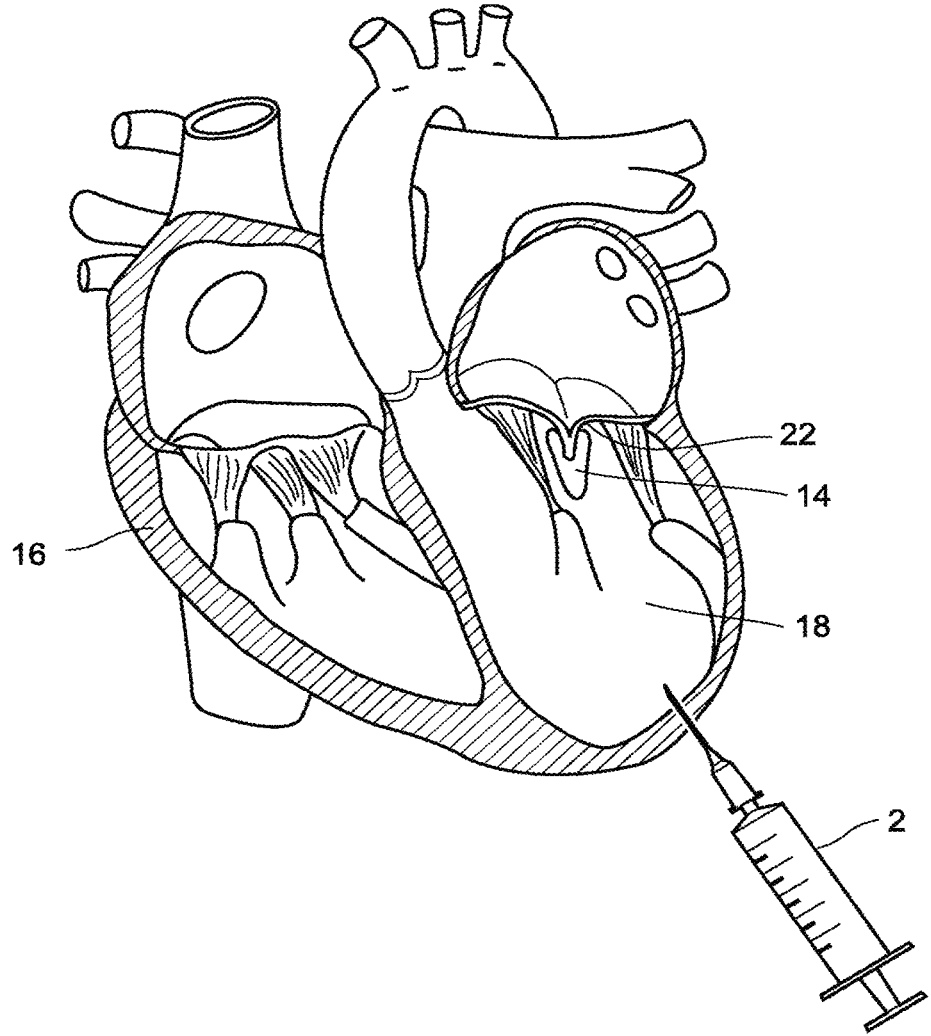
FIG. 4 illustrates a heart of a patient having a mitral clip at the mitral valve, wherein the transapical removal device of the present disclosure is being used to puncture the left ventricle of the heart.
Figure 5:
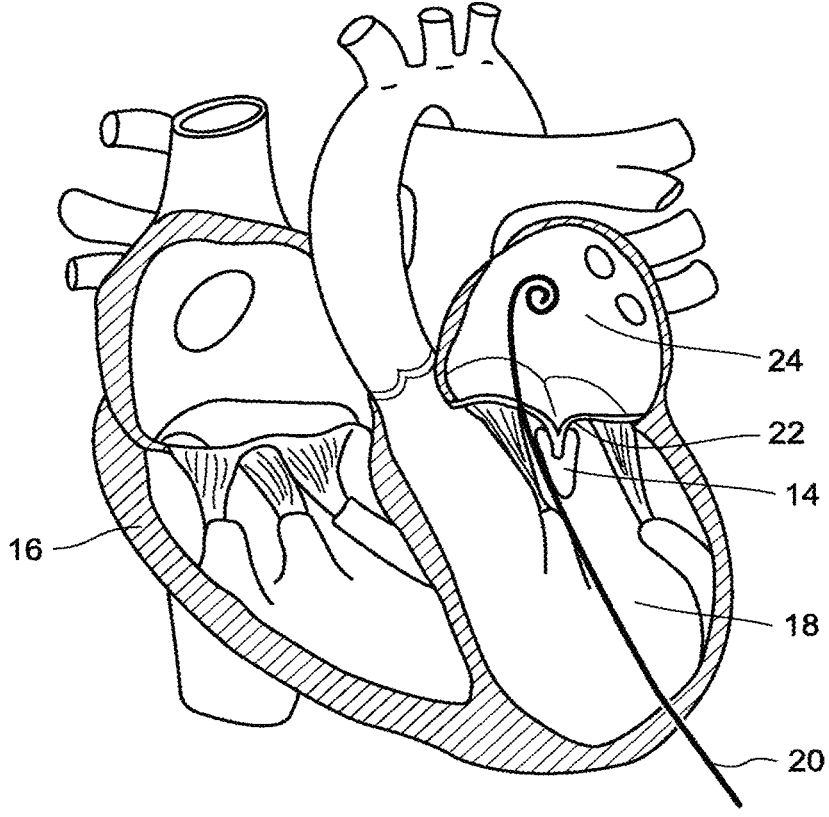
FIG. 5 illustrates the heart of the patient depicted in FIG. 4, wherein a guide wire of the transapical removal device of the present disclosure is being inserted through the puncture in the left ventricle, into the left ventricle, and up into the left atrium.
Figure 6:
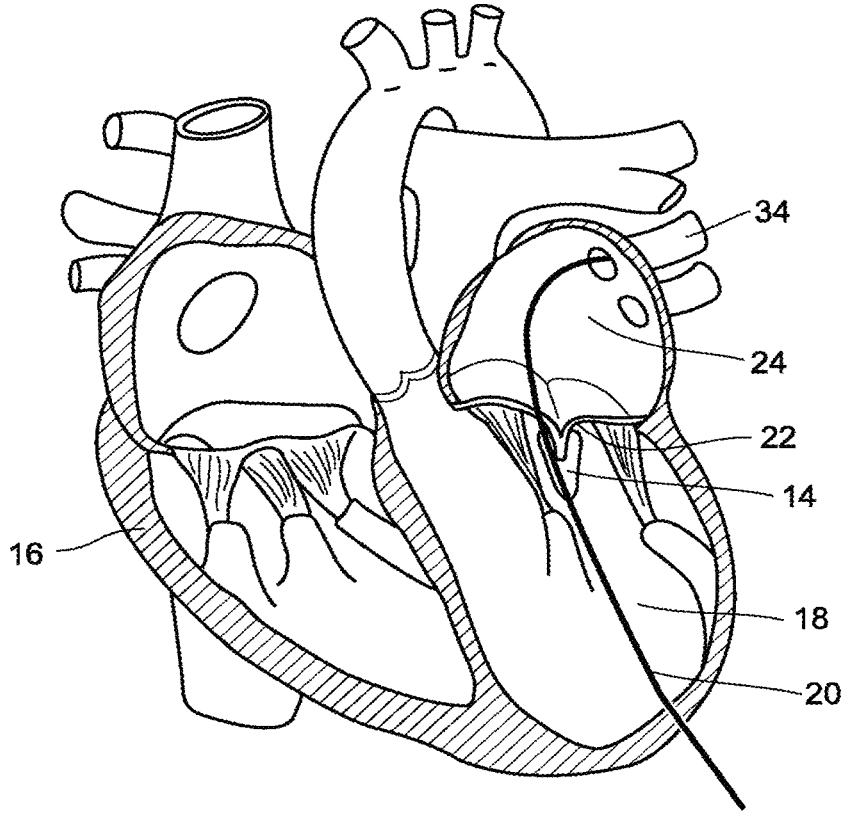
FIG. 6 illustrates the heart of the patient depicted in FIGS. 4 and 5, wherein a guide wire of the transapical removal device of the present disclosure is being inserted into a pulmonary vein.
Figure 7:
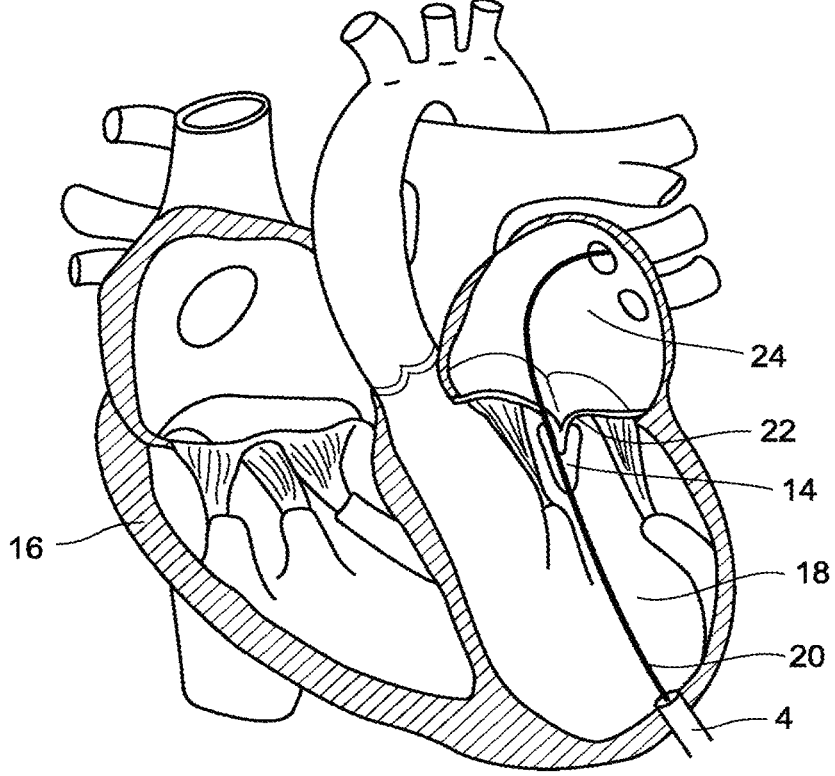
FIG. 7 illustrates the heart of the patient depicted in FIGS. 4-6, wherein a delivery catheter of the transapical removal device of the present disclosure is inserted into the left ventricle over the guide wire.
Figure 8:
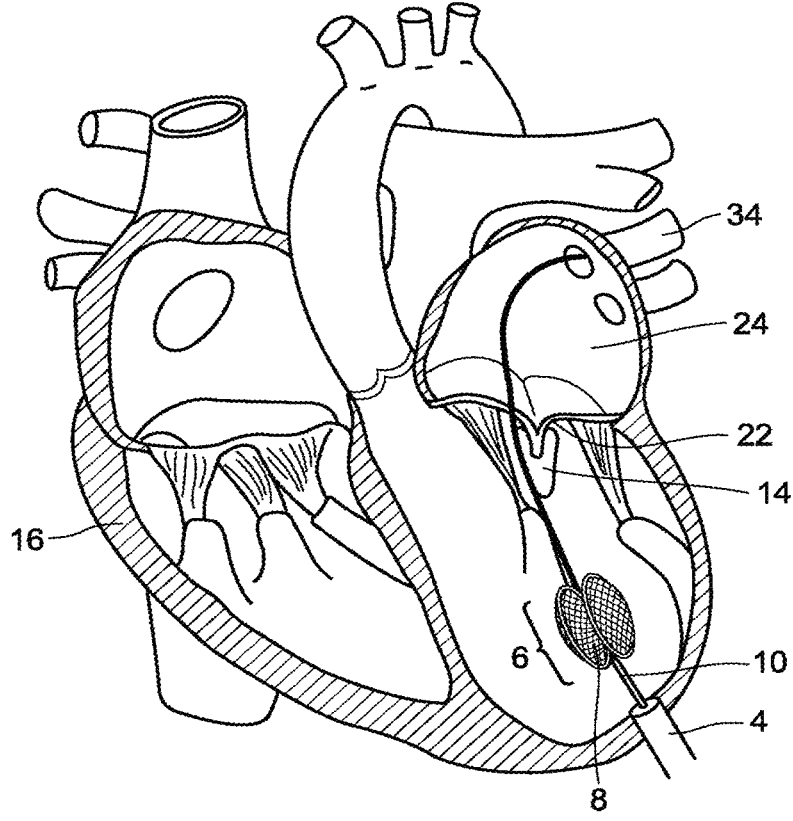
FIG. 8 illustrates the heart of the patient depicted in FIGS. 4-7, wherein a snare head is deployed from the delivery catheter.
Figure 9:
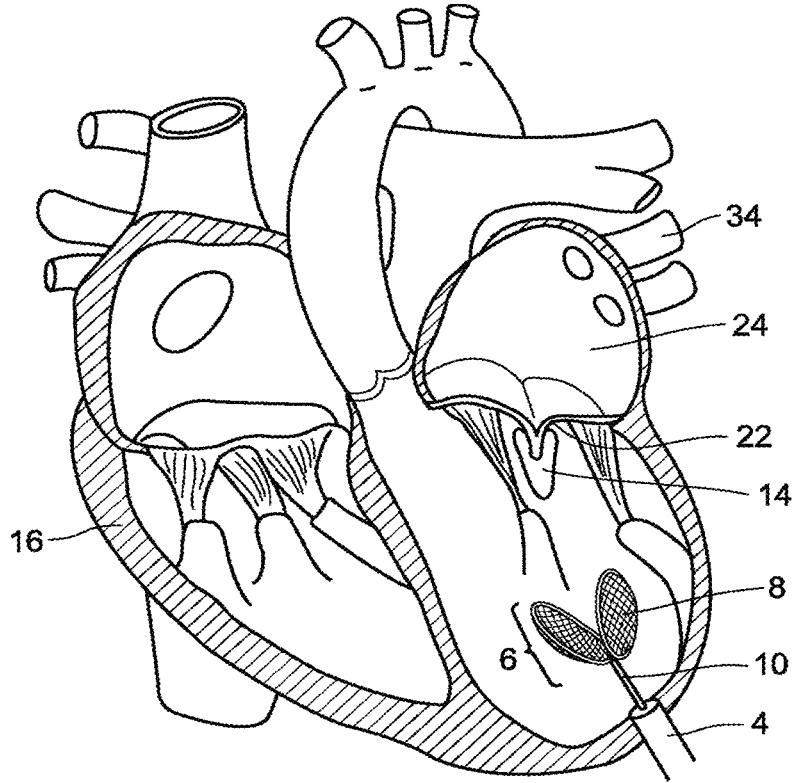
FIG. 9 illustrates the heart of the patient depicted in FIGS. 4-8, wherein the snare head is opened so that it can surround the mitral clip.
Figure 10:
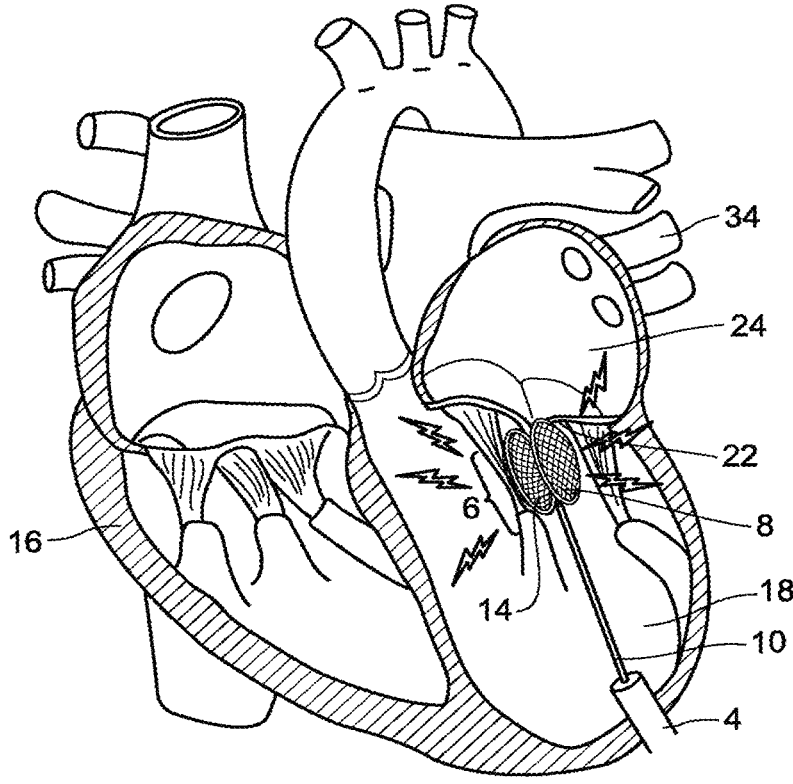
FIG. 10 illustrates the heart of the patient depicted in FIGS. 4-9, wherein the snare head is closed around the mitral clip, the tissue surrounding the mitral clip is ablated, and the mitral clip is captured in the snare head.

FIGS. 4-12 depict a transapical method of removing a mitral valve clip 14. This method could also be used to remove or alter an anterior leaflet of the mitral valve. In FIG. 4, a mitral valve clip 14 that has been pre-positioned on the mitral valve 22 to bind at least a portion of the mitral valve is depicted in a heart 16 of a patient. The transapical removal device 2 is used to puncture the left ventricle 18 of the heart 16. As shown in FIG. 5, a guide catheter 20 is then inserted into the left ventricle, through the mitral valve 22, and into the left atrium 24. As shown in FIG. 6, the guide catheter 20 may be inserted into a pulmonary vein 34. As shown in FIG. 7, using the guide catheter 20, the delivery catheter 4 is inserted into the left ventricle 18. As shown in FIG. 8, the snare head 6 is deployed from a collapsed state that allowed it to move through the delivery catheter 4 to a deployed state that allows it to capture the mitral valve clip 14. A snare head controller (not pictured) controls the transition of the snare head between the collapsed state and the deployed state. As shown in FIG. 9, the snare head 6 has a deployed basket 8 that opens to at least partially surround the pre-positioned mitral valve clip 14. The snare basket may include medical-grade plastic, medical-grade metal, or both. In some arrangements within the scope of the present disclosure, the snare head 6 may be made from a shape memory material such as nitinol in order to assist with deployment of the snare head 6. In other arrangements within the scope of the present disclosure, such as that shown in FIGS. 1A and 1B, the snare head 6 may include a spring that is compressed when the snare head 6 is in the collapsed state and at rest when the snare head 6 is in the deployed state, the spring configured to be compressed within the snare basket 8 unless the snare basket 8 is in the deployed state. As shown in FIG. 10, the snare basket 8 then closes around the mitral valve clip 14. In some arrangements, the snare head 6 may include magnets 36 (shown in FIGS. 3B and 3C) that cause the snare head basket 8 to close.

Once the snare basket is closed around the mitral valve clip 14, an ablation signal is provided to the ablation delivery catheters 10 and delivered to the tissue surrounding the mitral valve clip 14. In some arrangements within the scope of the present disclosure, the ablation delivery catheters 10 each have an electrode 12 provided on a proximal end for supplying radiofrequency energy to ablate tissue. The radiofrequency signal may be in the range of 250-500 kHz. An electrical source 42 (shown in FIGS. 1A and 1B) such as a battery, can be in communication with the electrodes 12, and a switch 44 may be provided that alternately permits and ceases to permit electrical current to flow from the electrical source to the electrodes. The switch may be controlled remotely. In other arrangements within the scope of the present disclosure, an optical fiber 46 (shown in FIG. 3C) is positioned at a proximal end of each ablation delivery catheter 10 to deliver a laser ablation signal to ablate tissue adjacent the mitral valve clip 14. In other arrangements, the ablation source may be a cryo-thermal source.

Figure 11:
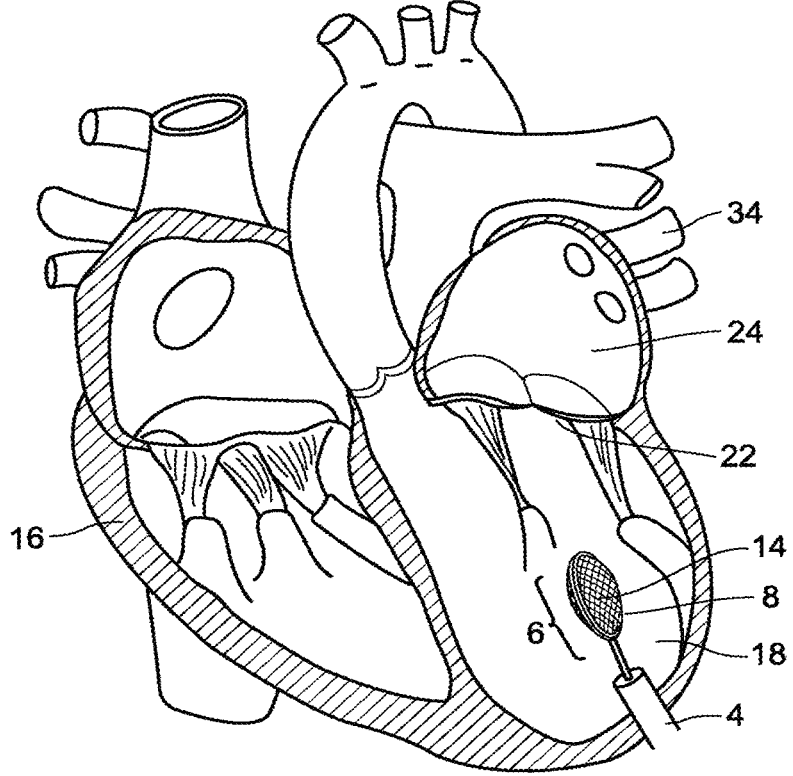
FIG. 11 illustrates the heart of the patient depicted in FIGS. 4-10, wherein the snare head is in a collapsed state after capturing the mitral clip.
Figure 12:
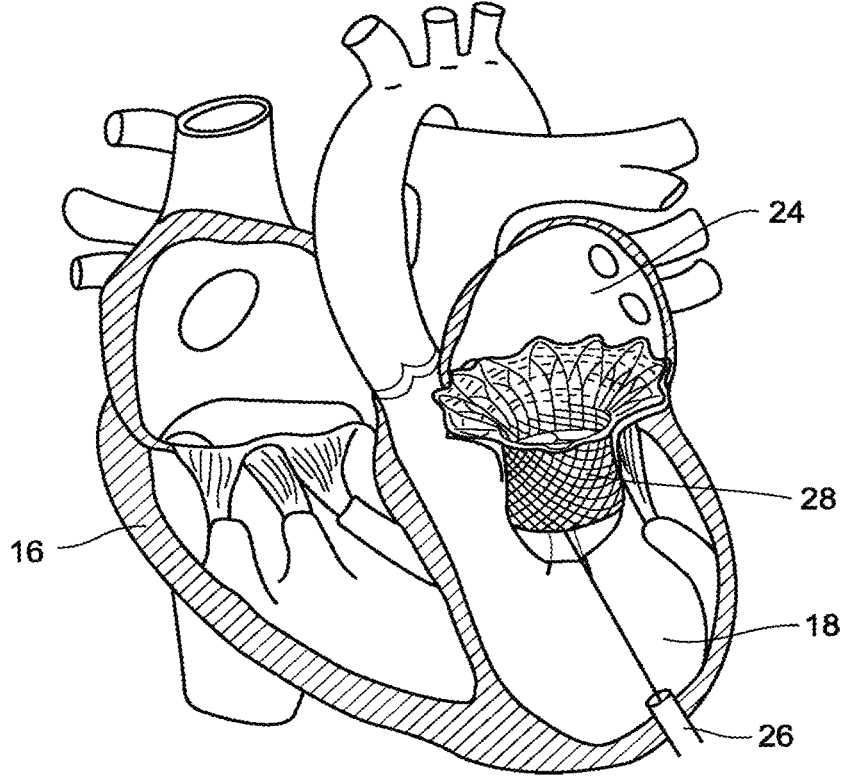
FIG. 12 illustrates the heart of the patient depicted in FIGS. 4-11, wherein a new transcatheter valve is deployed into the mitral valve through the delivery catheter.

The snare head controller controls the position and/or size of the snare basket 8 during the deployed state and also controls ablation source delivery to the tissue during the deployed state. The mitral valve clip 14 is then captured by the snare basket 8 of the snare head 6. As shown in FIG. 11, the snare head 6 assumes a collapsed state and is retracted into the delivery catheter 4. In some arrangements within the scope of the present disclosure, a retraction funnel (shown in FIGS. 1A and 1B) may be provided at a proximal end of the delivery catheter 4 to help forcibly return the snare head 6 to the collapsed state from the deployed state. In order to provide a functional mitral valve 22, a new transcatheter valve 28 may be deployed by a deployment mechanism 26, which includes the delivery catheter 4 in the arrangement depicted in FIG. 12.

Although the method of using a transapical removal device 2 depicted in FIGS. 4-12 is directed to removal of a mitral valve clip 14, the transapical removal device 2 could be used for other purposes, such as to remove or alter the anterior leaflet. A person having skill in the art would recognize that substantially the same steps as discussed above could be used for such purposes. Although the snare basket 8 is depicted as having a two-part snare basket in FIGS. 4-12, a single-part basket or a multi-part basket having more than two sides may be used. Further, the snare basket 8 may be configured in a variety of shapes, may. For example, the snare basket 8 may be open-ended at its distal and proximal ends for slidable removal of the captured tissue and/or clip, once the assembly is fully extracted from the subject. In other examples, the snare basket 8 may be continuous or otherwise sealed at the distal and proximal ends. In some examples, the snare basket 8 may have a flat configuration that facilitates removal or alteration of the anterior leaflet. In yet other examples, the ablation delivery catheters 10 may be secured to the snare basket 8 in a way that allows ablation of only a portion of an anterior leaflet, such as the center portion.

Figure 13:
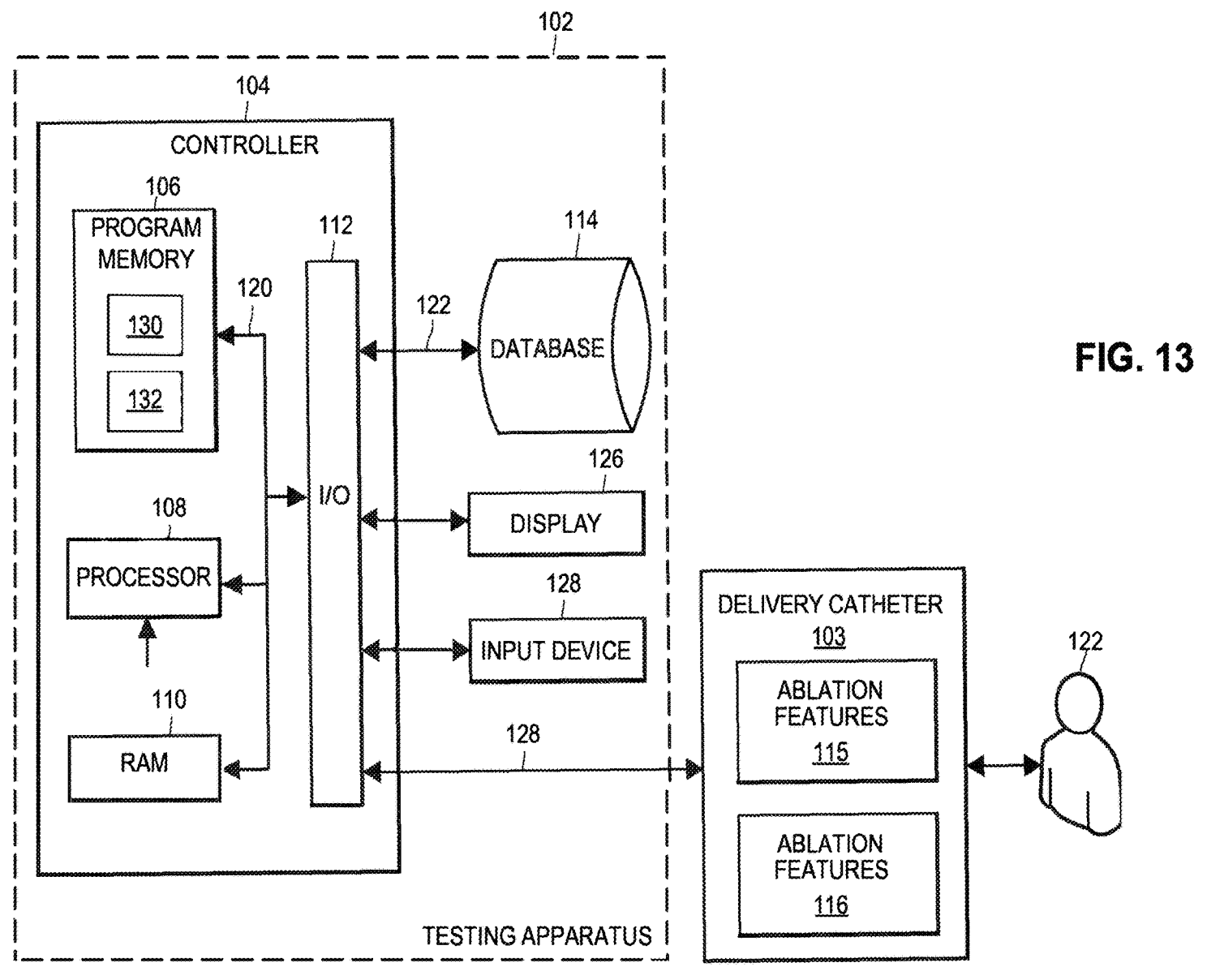

FIG. 13 is an example block diagram 100 illustrating the various components used in implementing an example arrangement of a method of using a transapical removal device as discussed herein. A transapical removal device may be inserted into a patient 122 via a delivery catheter 103 that may include ablation features 115 and sensors 116. The removal device may be controlled by a control system 102 having a snare head controller 104 operatively connected to various elements of the system 102. The control system 102 may be a standalone transapical device removal system, such as a portable machine at a point of care position. In other examples, the control system 102 may be implemented into existing control systems, such as an existing ablation control system, having an ablation pump, a catheter sensor/ switching control system, etc. While not shown, the control system 102 may include mechanical controls, such as foot controls and hand controls for providing full or partial mechanical operation of catheter delivery, snare head deployment, and ablation features. It will be appreciated that some portion of the control system 102, whether electronic and/or mechanical portions, may be distributed into a control handle for the delivery catheter of the removal device, for snare head, sensor, and/or catheter control.

In the illustrated example, the control system 102 includes a database 114 (via a link 122 connected to an input/output (I/O) circuit 112) for storing collect data, such as historical data from the controller 104 and/or from external data sources, such as historical data collected from other medical devices and medical databases. That is, it should be noted that, while not shown, additional databases may be linked to the snare head controller 104 in a known manner.

The snare head controller 104 includes a program memory 106, the processor 108 (may be called a microcontroller or a microprocessor), a random-access memory (RAM) 110, and the input/output (I/O) circuit 112, all of which are interconnected via an address/data bus 120. It should be appreciated that although only one microprocessor 108 is shown, the snare head controller 104 may include multiple microprocessors 108. Similarly, the memory of the controller 104 may include multiple RAMs 110 and multiple program memories 106. Although the I/O circuit 112 is shown as a single block, it should be appreciated that the I/O circuit 112 may include a number of different types of I/O circuits. The RAM(s) 110 and the program memories 106 may be implemented as semiconductor memories, magnetically readable memories, and/or optically readable memories, for example. A link 124 may operatively connect the controller 104 to the sensors 116 through the I/O circuit 112.

The program memory 106 and/or the RAM 110 may store various applications (i.e., machine readable instructions) for execution by the microprocessor 108. For example, an operating system 130 may generally control the operation of the control system 102 and provide a user interface to the control system 102 to implement the removal processes described herein. The program memory 106 and/or the RAM 110 may also store a variety of subroutines 132 for accessing specific functions of the testing apparatus 102. By way of example, and without limitation, the subroutines 132 may include, among other things: a subroutine for controlling ablation of mitral valve tissue, a subroutine for controlling activation of a snare head from a first collapsed state for delivery to the mitral value, to a deployed state for snaring the mitral valve clip, and then to a second collapsed state for removing the capture mitral valve clip, as well as other subroutines, for example, implementing software keyboard functionality, interfacing with other hardware in the computer system 102, etc. The program memory 106 and/or the RAM 110 may further store data related to the configuration and/or operation of the transapical removal device, and/or related to the operation of one or more subroutines 132. In addition to the controller 104, the control system 102 may include other hardware resources.

The control system 102 may also include various types of input/output hardware such as a visual display 126 and input device(s) 128 (e.g., keypad, keyboard, etc.). In an arrangement, the display 126 is touch-sensitive, and may cooperate with a software keyboard routine as one of the software routines 132 to accept user input. It may be advantageous for the testing apparatus to communicate with broader medical analysis networks or medical treatment networks (not shown) through any of a number of known networking devices and techniques (e.g., through a commuter network such as a hospital or clinic intranet, the Internet, etc.). For example, the control system 102 may be connected to a medical records database, hospital management processing system, health care professional terminals (e.g., doctor stations, nurse stations), patient monitoring systems, automated drug delivery systems. Accordingly, the disclosed arrangements may be used as part of an automated closed loop system or as part of a decision assist system.

Figure 14A:
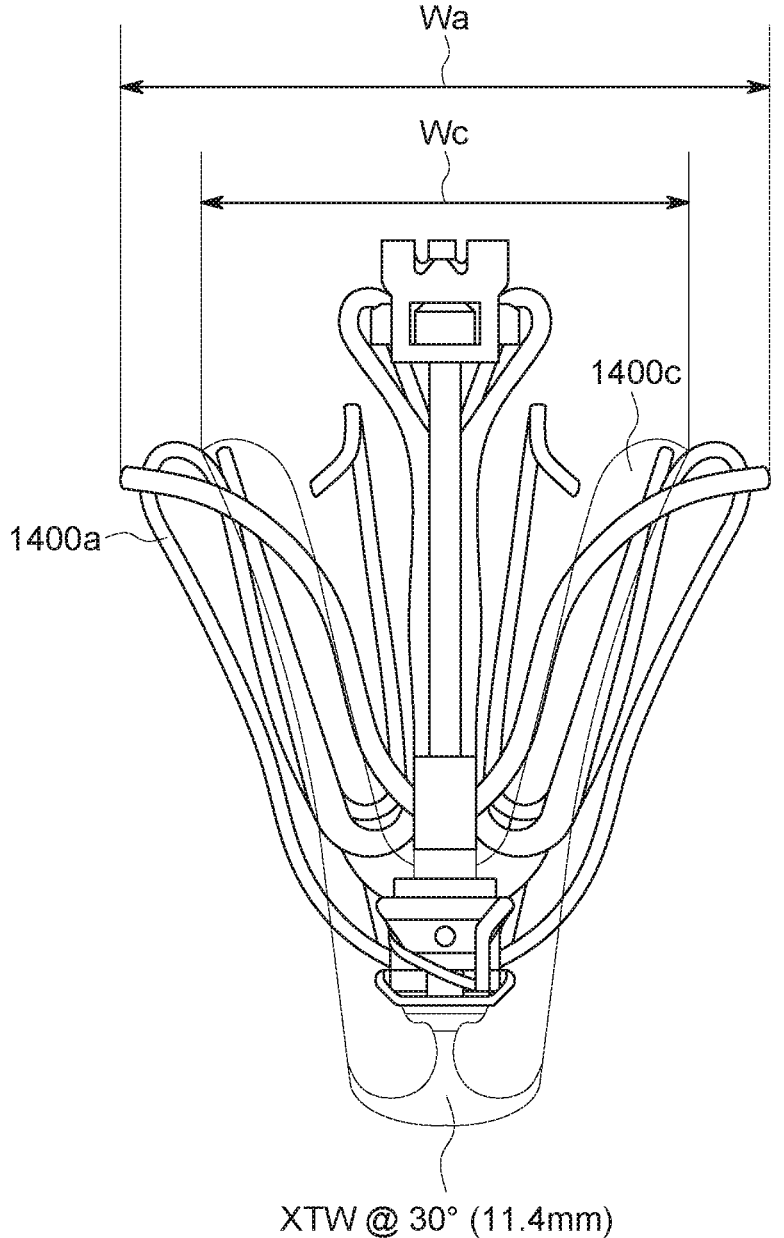
FIG. 14A illustrates a comparison of a first, wider exemplary valve clip and a second, narrower exemplary valve clip.

Devices and methods for removing a valve clip pre-positioned on a heart leaflet can be selected according to the valve clip to be removed. For purpose of example and as described above, different valve clips can have different cross-sectional profiles, and devices and methods for removing a respective valve clip can be selected according to the valve clip's profile. For purpose of example and illustration and not limitation FIG. 14A depicts a first exemplary valve clip 1400a in an implanted condition in solid line laid over a second exemplary valve clip 1400c in an implanted condition depicted in phantom line for purpose of comparison. For purpose of illustration and not limitation, the first exemplary valve clip 1400a is a representation of a Pascal valve clip as commercialized by Edwards Lifesciences Corporation, and the second exemplary valve clip 1400c is a representation of a MitraClip valve clip as commercialized by applicants. As shown, the first valve clip 1400a has an implanted width Wa when the valve clip 1400a is in an implanted condition, and the second exemplary valve clip 1400c has an implanted width Wc when the valve clip 1400c is in an implanted condition. As shown, the first exemplary valve clip 1400a has a larger implanted width Wa than the second exemplary valve clip 1400c, Wc. As described further herein, a valve clip having a smaller width or profile can be desirable, such as for example, to enable removal of the clip from the heart through a smaller diameter lumen.

As described further herein, the profile of exemplary clip 1400a can be changed, such as by manipulating the clip, which can facilitate removal of the clip 1400a from the heart. Exemplary clip 1400a is depicted in an implanted condition in FIG. 14B. Exemplary clip 1400a can include a first portion 1408a and a second portion 1408b, and the clip 1400a can grip native heart valve leaflets between the first portion 1408a and the second portion 1408b in the implanted condition. The first portion 1408a can be positioned on a first side of a native heart valve and the second portion 1408b can be positioned on a second, opposite side of a native heart valve. For example, and as embodied herein, the first portion 1408a can be positioned on a ventricular side of a native mitral valve and the second portion 1408b can be positioned on an atrial side of a native mitral valve and native mitral valve leaflets 1410 can be gripped between the first portion 1408a and the second portion 1408b. Exemplary clip 1400a has an implanted width W1 in the implanted condition.

Figure 14B:
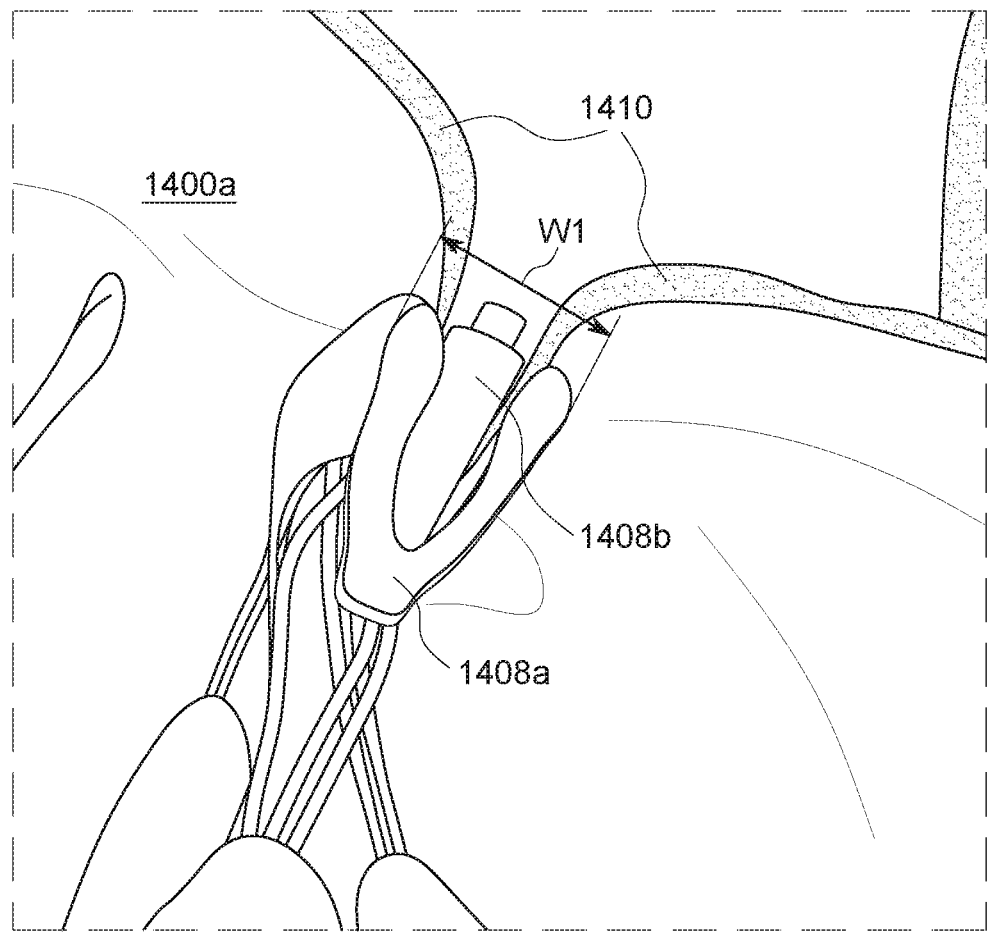
FIG. 14B illustrates a heart valve clip pre-positioned on a heart valve leaflet in an implanted condition.
Figure 14C:
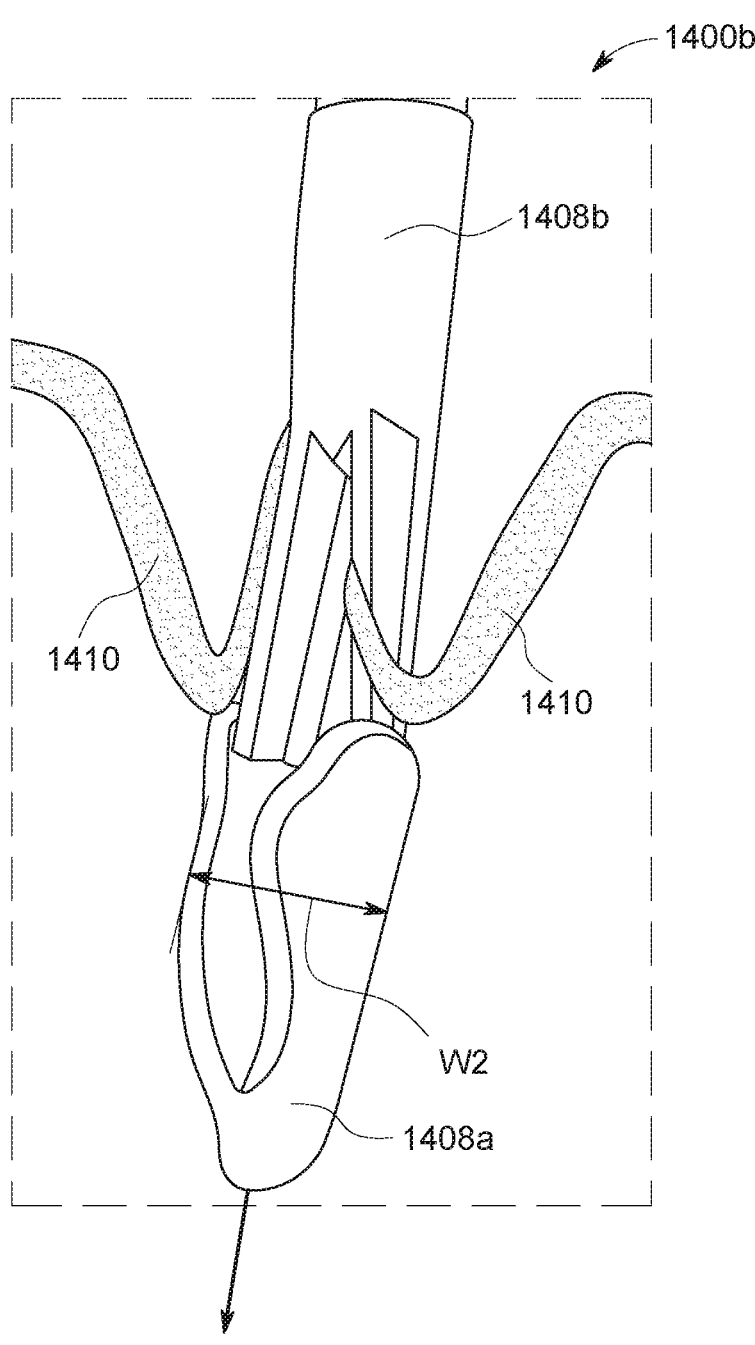
FIG. 14C illustrates a heart valve clip pre-positioned on a heart valve leaflet in an elongated condition.

FIG. 14C depicts exemplary clip 1400a in an elongated condition. As described further herein, clip 1400a can be manipulated from the implanted condition to the elongated condition. The clip 1400a has an elongated width W2 in the elongated condition. The elongated width W2 is less than the implanted width W1. As described further herein, the smaller profile or width of the clip 1400a in the elongated condition can, for example, facilitate removal of the clip 1400a from the heart.

In accordance with an aspect of the disclosed subject matter, devices and methods are provided for manipulating and removing a valve clip pre-positioned on a heart leaflet. Devices in accordance with this aspect of the disclosed subject matter include a delivery catheter having a distal end portion configured to be positioned near a heart valve. The devices also include a grasping tool deployable from the distal end portion of the delivery catheter. The grasping tool is configured to grasp and manipulate a valve clip from an implanted condition to an elongated condition. The valve clip in the elongated condition has an elongated width which is less than an implanted width of the valve clip in the implanted condition. The devices also include a removal tool extendable relative to the distal end portion of the delivery catheter. The removal tool is configured to at least partially surround the valve clip in the elongated condition and to remove the valve clip from the heart valve leaflet.

FIGS. 15A-15D depict an exemplary device 1500 for removing a valve clip pre-positioned on a heart leaflet 1510 in accordance with an aspect of the disclosed subject matter. The device 1500 includes a delivery catheter 1502 having a distal end portion 1502a configured to be positioned near a heart valve. The delivery catheter 1502 can be configured to be positioned near a heart valve using any suitable delivery technique. For example, the delivery catheter 1502 can be configured for trans vascular delivery to and positioning near a heart valve. Additionally or alternatively, the delivery catheter 1502 can be configured for transapical delivery to and positioning near a heart valve. For example and as embodied herein, the heart valve can be a mitral valve and the delivery catheter 1502 can be configured to for transapical delivery to the mitral valve. The delivery catheter 1502 can have any suitable configuration. For example, the delivery catheter 1502 can be steerable and can include an elongate shaft 1524 and a handle to move the elongate shaft 1524 relative to the handle. Steerable catheters are known in the art and can include, for example, a drive mechanism, which can include, for example and not limitation, at least one of threading and a rotatable knob to advance the delivery catheter 1502 along the threading, a push-pull lever, or a plunger.

The device 1500 further includes a grasping tool 1504 deployable from the distal end portion 1502a of the delivery catheter 1502. The grasping tool 1504 is configured to grasp and manipulate a valve clip 1508 from an implanted condition to an elongated condition, the valve clip 1508 in the elongated condition having an elongated width W2 less than an implanted width W1 of the valve clip 1508 in the implanted condition. As described further herein, the grasping tool 1504 can have any suitable configuration for grasping and manipulating the valve clip 1508. For example and not limitation, the grasping tool can include one or more hooks, pinchers, grippers, jaws, graspers, fingers, snares, wires, or any other suitable element for grasping and manipulating the valve clip. For example and as embodied herein, the grasping tool 1504 can include two or more opposing hooks 1516 configured to be moveable between an open state 1504a and a closed state 1504b. The grasping tool 1504 is depicted in an open state 1504a in FIG. 15B and in a closed state 1504b in FIG. 15C. In the open state 1504a, the opposing hooks 1516 can be spaced apart at their respective distal ends 1516a, and in the closed state 1504b, the respective distal ends 1516a can be adjacent each other.

For purpose of example and as embodied herein, the opposing hooks 1516 can be biased towards the open state 1504a when deployed from the distal end portion 1502a of the delivery catheter 1502. As an example and not limitation, the hooks can be spring biased. The grasping tool 1504 can be deployed using any suitable means. For example and not limitation, a sheath or lumen can surround the grasping tool 1504 when the grasping tool 1504 is in a closed state 1504b, and the sheath or lumen can be retracted to deploy the grasping tool 1504 to an open state 1504a. Additionally or alternatively, and as embodied herein, deploying the grasping tool 1504 can include advancing the grasping tool 1504 distally from the distal end portion 1502a of the delivery catheter 1502. The opposing arms 1516 can be biased towards the open state 1504a, such as by a spring or any other suitable means, and as the opposing arms 1516 are deployed from the distal end portion 1502a the opposing arms 1516 can move towards the open state. As further embodied herein, the opposing arms 1516 can be urged toward the closed state 1504b when the grasping tool 1504 is retracted relative to the distal end portion 1502a of the delivery catheter 1502.

The grasping tool 1504 can be made from any suitable material, such as for example nitinol, steel, cobalt chrome, polymers, ceramics, or any other suitable material. Additionally or alternatively, the grasping tool 1504 can be made from undulating wireforms or machined components with integrated spring-hinges. The grasping tool 1504 can have any suitable shape to facilitate grasping and manipulating the valve clip 1508. For example and as described further herein, the grasping tool 1504 can include one or more snares 1518. Additionally or alternatively, and as embodied herein, the grasping tool 1504 can include one or more hooks 1516. The hooks 1516 can be forked, split, curved, bent, tapered, sharp, blunt, smoothed (electro-polished), roughened, hardened, or annealed. Additionally or alternatively, the hooks 1516 can be symmetric or asymmetric.

Figures 15A, 15B, 15C, 15D:
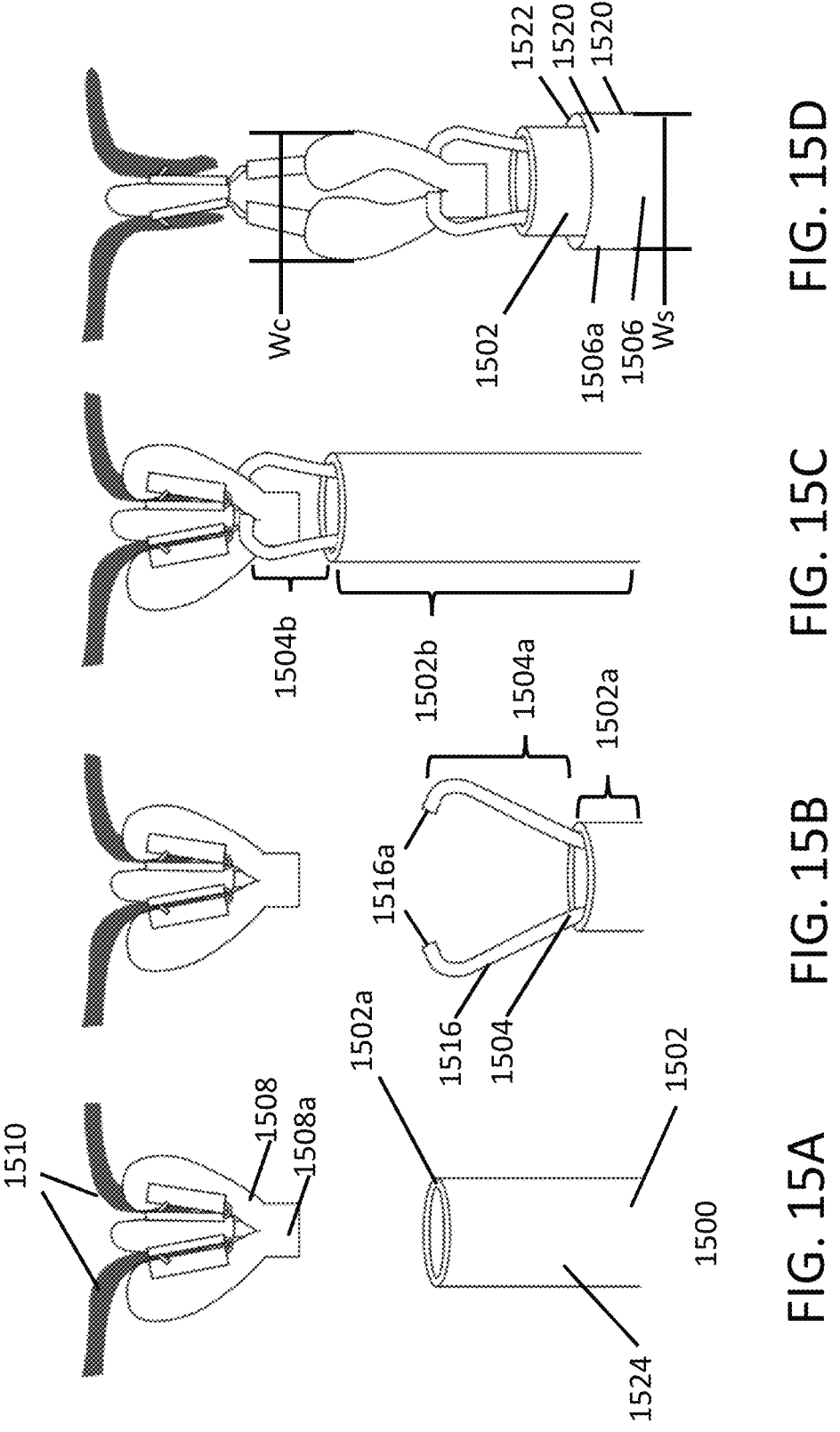
FIG. 15A illustrates a valve clip pre-positioned on a heart valve leaflet and an exemplary removal device in accordance with an aspect of the disclosed subject matter with a delivery catheter of the removal device positioned near the heart valve.
FIG. 15B illustrates the exemplary removal device of FIG. 15A with a grasping tool deployed from a distal end portion of the delivery catheter, wherein the grasping tool comprises opposing hooks.
FIG. 15C illustrates the exemplary removal device of FIG. 15A with the grasping tool grasping a first portion of the valve clip with the valve clip in an implanted condition.
FIG. 15D illustrates the exemplary removal device of FIG. 15A with the grasping tool grasping a first portion of the valve clip with the valve clip in an elongated condition.
Figures 16A, 16B, 16C, 16D, 16E:
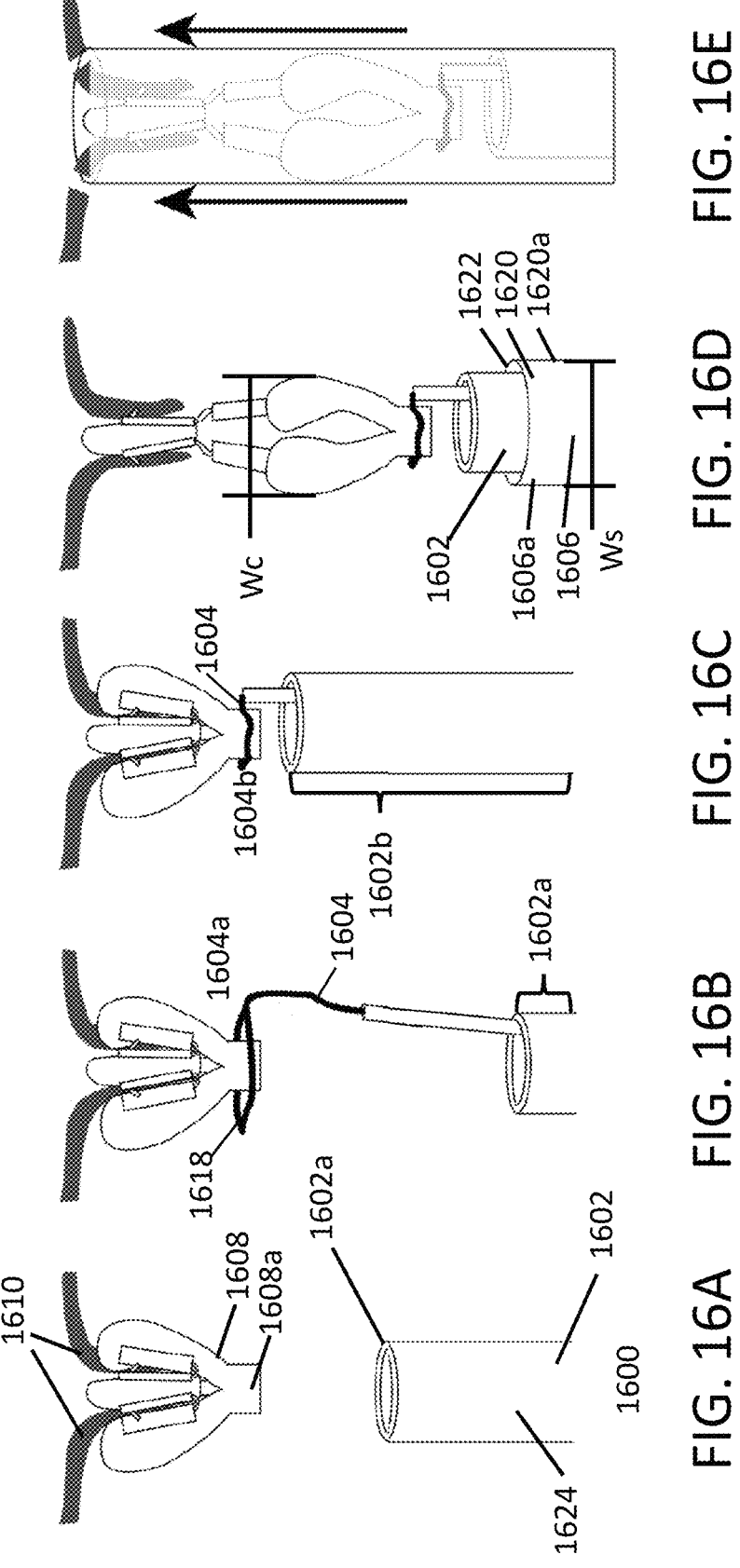
FIG. 16A illustrates a valve clip pre-positioned on a heart valve leaflet and an exemplary removal device in accordance with an aspect of the disclosed subject matter with a delivery catheter of the removal device positioned near the heart valve.
FIG. 16B illustrates the exemplary removal device of FIG. 16A with a grasping tool deployed from a distal end portion of the delivery catheter, wherein the grasping tool comprises a snare.
FIG. 16C illustrates the exemplary removal device of FIG. 16A with the grasping tool grasping a first portion of the valve clip with the valve clip in an implanted condition.
FIG. 16D illustrates the exemplary removal device of FIG. 16A with the grasping tool grasping a first portion of the valve clip with the valve clip in an elongated condition.
FIG. 16E illustrates the exemplary removal device of FIG. 16A with the removal tool extended relative to the distal end portion of the delivery catheter and at least partially surrounding the valve clip in the elongated condition.
Figures 17A, 17B, 17C, 17D:
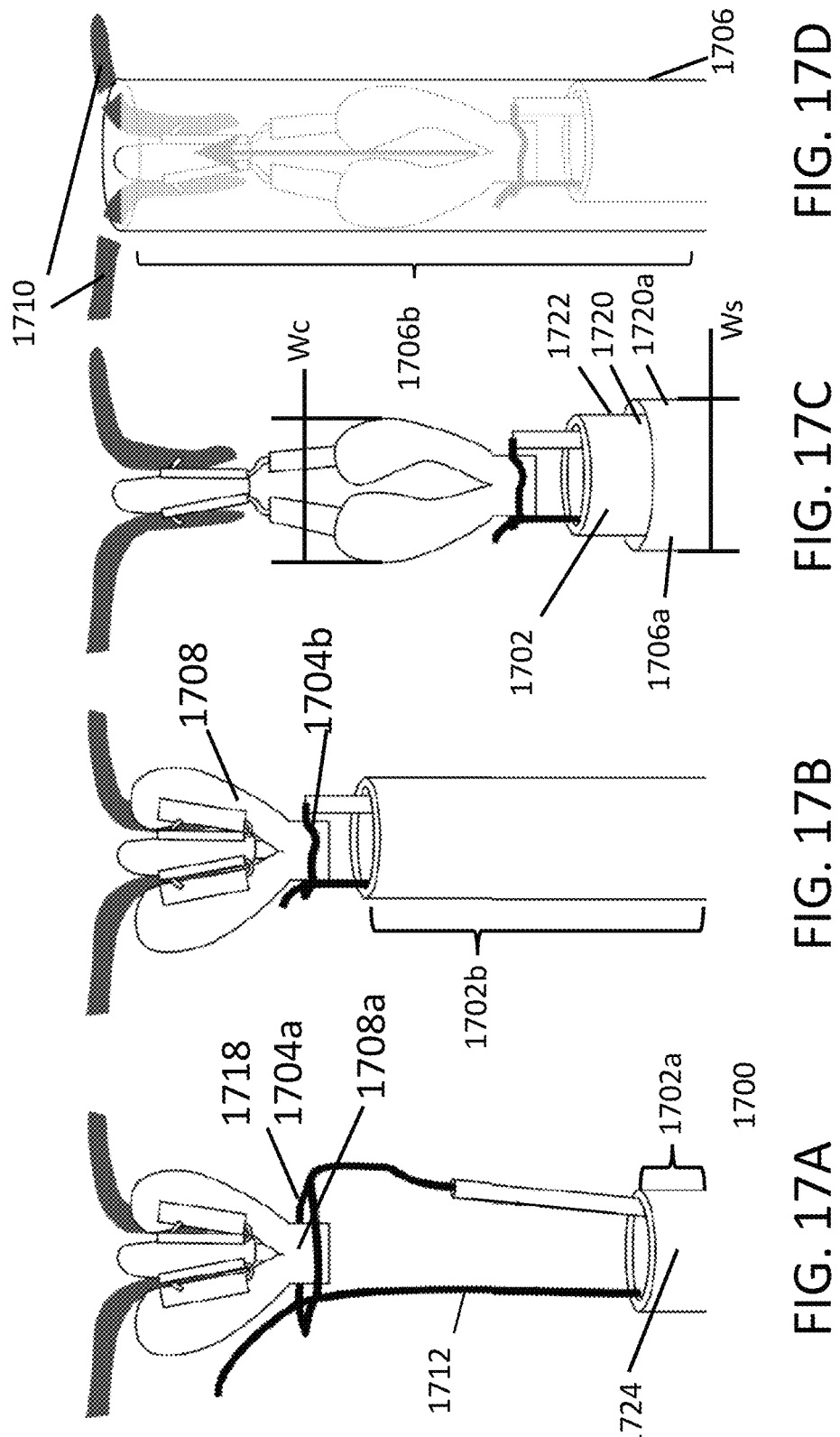
FIG. 17A illustrates the exemplary removal device of FIG. 16B with the snare deployed from a distal end portion of the delivery catheter, and the grasping tool further comprises an alignment wire positioned within the loop opening.
FIG. 17B illustrates the exemplary removal device of FIG. 17A with the grasping tool grasping a first portion of the valve clip with the valve clip in an implanted condition.
FIG. 17C illustrates the exemplary removal device of FIG. 17A with the grasping tool grasping a first portion of the valve clip with the valve clip in an elongated condition.
FIG. 17D illustrates the exemplary removal device of FIG. 17A with the removal tool extended relative to the distal end portion of the delivery catheter and at least partially surrounding the valve clip in the elongated condition.
Figures 18A, 18B, 18C, 18D:
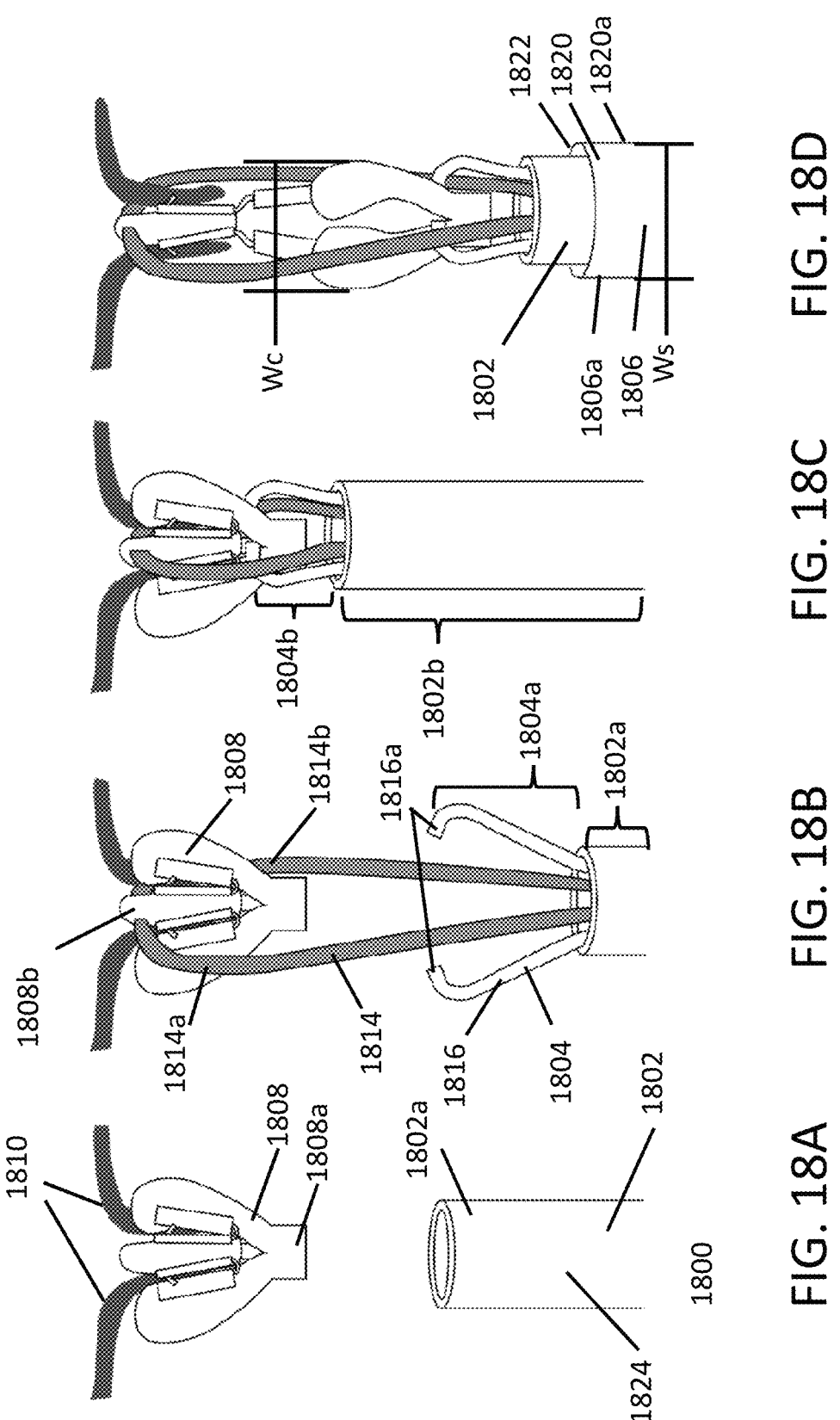
FIG. 18A illustrates a valve clip pre-positioned on a heart valve leaflet and an exemplary removal device in accordance with an aspect of the disclosed subject matter with a delivery catheter of the removal device positioned near the heart valve.
FIG. 18B illustrates the exemplary removal device of FIG. 18A with a grasping tool deployed from a distal end portion of the delivery catheter and a stabilizing tool holding the second portion of the valve clip.
FIG. 18C illustrates the exemplary removal device of FIG. 18A with the grasping tool grasping a first portion of the valve clip with the valve clip in an implanted condition and the stabilizing tool holding the second portion of the valve clip.
FIG. 18D illustrates the exemplary removal device of FIG. 18A with the grasping tool grasping a first portion of the valve clip with the valve clip in an elongated condition and a stabilizing tool tool holding the second portion of the valve clip.

The device 1500 further includes a removal tool 1506 extendable relative to the distal end portion 1502a of the delivery catheter 1502. The removal tool 1506 is configured to at least partially surround the valve clip 1508 with the valve clip 1508 in the elongated condition and to remove the valve clip 1508 from the heart valve leaflet 1510. FIG. 15D illustrates valve clip 1508 in an elongate condition with the grasping tool 1504 grasping a first portion 1508a of the valve clip 1508. In accordance with an aspect of the disclosed subject matter, the removal tool 1506 is extendable relative to the distal end portion 1502a of the delivery catheter 1502. The removal tool 1506 can have any suitable configuration. Additionally or alternatively and embodied herein, the removal tool 1506 can include a sheath 1520 defining a sheath lumen 1520a to at least partially surround the valve clip 1508 with the valve clip 1508 in the elongated condition. For example, the sheath lumen 1520a can have a sheath lumen diameter Ws and the sheath lumen diameter can be greater than the elongated width We of the vale clip 1508 in the elongated condition. As embodied herein, the delivery catheter 1502 and the removal tool 1506 can define concentric lumens, and the delivery catheter 1502 can be at least partially disposed within the removal tool 1506. Additionally or alternatively the delivery catheter 1502 can define an outermost lumen and the removal tool 1506 can be at least partially disposed within the delivery catheter 1502.

For example and not limitation, the removal tool 1502 can include a blade. Additionally or alternatively, the removal tool 1502 can include an ablation device which operates as described above. For example and not limitation, the removal tool 1502 can include a blade and/or ablation device disposed at the distal end 1506a of the removal tool 1506. As further embodied herein, the sheath 1520 can include a blade 1522 at a distal end 1506a of the sheath 1520. For example and as embodied herein, the blade 1522 can be defined around the perimeter of the distal end 1506a of the sheath 1520.

As described further herein, the removal tool 1506 is extendable relative to the distal end portion 1502a of the delivery catheter 1502, and the removal tool 1506 is configured to at least partially surround the valve clip 1508 in the elongated condition and to remove the valve clip 1508 from the heart valve leaflet 1510. For example and as embodied herein, the sheath 1520 can be extended relative to the distal end portion 1502a of the delivery catheter 1502 with the valve clip 1508 in the elongated condition. As embodied herein, the sheath lumen 1520a can at least partially surround the valve clip 1508 with the removal tool 1506 extended. As further embodied herein, the blade 1522 of the removal tool 1506 can cut through heart valve leaflet tissue 1510 as the removal tool 1506 extends and as the removal tool 1506 at least partially surrounds the valve clip 1508. As described further herein, with the valve clip 1508 removed or resected from the heart valve leaflet 1510, the valve clip 1508 can be removed from the heart.

FIGS. 16A-16E depict an exemplary device 1600 for removing a valve clip pre-positioned on a heart leaflet in accordance with an aspect of the disclosed subject matter. The device 1600 includes a delivery catheter 1602 having a distal end portion 1602a configured to be positioned near a heart valve. The exemplary device 1600 further includes a grasping tool deployable from the distal end portion of the delivery catheter. The grasping tool is configured to grasp and manipulate a valve clip from an implanted condition to an elongated condition, the valve clip in the elongated condition having an elongated width less than an implanted width of the valve clip in the implanted condition. The exemplary device 1600 further includes a removal tool extendable relative to the distal end portion of the delivery catheter. The removal tool is configured to at least partially surround the valve clip in the elongated condition and to remove the valve clip from the heart valve leaflet.

For purpose of example and as shown in FIGS. 16A-E, the grasping tool 1604 can include a snare 1618. The snare 1618 can have an open state 1604a; when the delivery catheter 1602 is advanced, the snare 1618 can be moved to a closed state 1604b to grasp the first portion 1608a of the valve clip 1608. The snare 1618 can have a larger diameter in the open state 1604a than in the closed state 1604b. The first portion 1608a of the valve clip can be disposed within the ventricle of the patient's heart. For example and as embodied herein, the snare 1618 can define a loop which can shrink in diameter to grasp the valve clip 1608 when the snare 1618 is moved from the open state 1604*a* to the closed state 1604*b*.

FIGS. 17A-D depict an exemplary device 1700 for removing a valve clip pre-positioned on a heart leaflet in accordance with an aspect of the disclosed subject matter. The device 1700 includes a delivery catheter 1702 having a distal end portion 1702*a* configured to be positioned near a heart valve. The exemplary device 1700 further includes a grasping tool 1704 deployable from the distal end portion 1702*a* of the delivery catheter 1702. The grasping tool 1704 is configured to grasp and manipulate a valve clip 1708 from an implanted condition to an elongated condition, the valve clip 1708 in the elongated condition having an elongated width less than an implanted width of the valve clip 1708 in the implanted condition. The exemplary device 1700 further includes a removal tool 1706 extendable relative to the distal end portion 1702*a* of the delivery catheter 1702. The removal tool 1706 is configured to at least partially surround the valve clip 1708 in the elongated condition and to remove the valve clip 1708 from the heart valve leaflet 1710.

As depicted in FIGS. 17A-D, some embodiments can include an alignment wire 1712 which can be positioned between the snare 1718 and the first portion 1708*a* of the valve clip 1708 when the snare is cinched from the open state 1704*a* to the closed state 1704*b* such that the alignment wire 1712 is trapped between the closed snare 1718 and the first portion 1708*a* of the valve clip 1708. The alignment wire 1712 can provide support to the snare 1718, align the snare 1718 relative to the valve clip 1708, and provide extra grip to the snare 1718. One having skill in the art will appreciate that other embodiments may also be possible. For purpose of example and as embodied herein, the grasping tool 1704 can be controlled independently of the delivery catheter 1702 to advance and retract.

FIGS. 18A-D depict an exemplary device 1800 for removing a valve clip pre-positioned on a heart leaflet in accordance with an aspect of the disclosed subject matter. The device 1800 includes a delivery catheter 1802 having a distal end portion 1802*a* configured to be positioned near a heart valve. The exemplary device 1800 further includes a grasping tool 1804 deployable from the distal end portion 1802*a* of the delivery catheter 1802. The grasping tool 1804 is configured to grasp and manipulate a valve clip 1808 from an implanted condition to an elongated condition, the valve clip 1808 in the elongated condition having an elongated width less than an implanted width of the valve clip 1808 in the implanted condition. The exemplary device 1800 further includes a removal tool 1806 extendable relative to the distal end portion 1802*a* of the delivery catheter 1802. The removal tool 1806 is configured to at least partially surround the valve clip 1808 in the elongated condition and to remove the valve clip 1808 from the heart valve leaflet 1810.

The removal device 1800 can include a stabilizing tool 1814 as shown in FIGS. 18A-D. The stabilizing tool 1814 can include opposing arms 1814*a*, 1814*b* which are moveable between an open condition and a closed condition. For example and as embodied herein, stabilizing tool 1814 can hold the second portion 1808*b* of the valve clip 1808, which can be generally disposed within the atrium of the patient's heart and opposite first portion 1808*a*, such that the stabilizing tool 1814 remains stationary or moves proximally while the grasping tool 1804 moves distally; thus, the stabilizing tool 1814 can provide a counter-force to the force applied by the grasping tool 1804 which can assist in transitioning the valve clip 1808 from the implanted condition to the elongated condition. The counter-force applied by the stabilizing tool 1814 can oppose the force applied by the grasping tool 1804. For purpose of example and as embodied herein, the stabilizing tool 1814 can include hooks 1814*a*, 1814*b* which can, but need not be, rotated approximately 90 degrees relative to the hooks 1816 of the grasping tool 1804; one having skill in the art will appreciate that other embodiments may also be possible. Once deployed, the stabilizing tool 1814 can provide additional support when transitioning the valve clip 1808 from the implanted condition to the elongated condition. Therefore, the stabilizing tool 1814 can be used when the integrity of the heart valve leaflet 1810 is poor such that using the grasping tool 1804 alone may cause unintended damage to the heart valve leaflet 1810. The stabilizing tool 1814 can also be utilized in cases where the repair device 1808 is only attached to a single leaflet 1810.

In accordance with another aspect of the disclosed subject matter, methods for removing a valve clip pre-positioned on a heart valve leaflet are provided. Methods for removing a valve clip pre-positioned on a heart valve leaflet include delivering, to a chamber of a patient's heart, a removal device including a delivery catheter, a grasping tool, and a removal tool. The removal device can include any of the features described herein. Methods for removing a valve clip pre-positioned on a heart valve leaflet further include deploying the grasping tool from the delivery catheter to grasp the valve clip and manipulating the valve clip from an implanted condition to an elongated condition. As described above, the valve clip in the elongated condition has an elongated width less than an implanted width of the valve clip in the implanted condition. Methods for removing a valve clip pre-positioned on a heart valve leaflet further include at least partially surrounding the valve clip in the elongated condition with the removal tool, and removing the valve clip from the heart valve leaflet using the removal tool.

An exemplary method in accordance with an aspect of the disclosed subject matter is described with reference to the exemplary device 1500 depicted in FIGS. 15A-D. The method includes delivering, to a chamber of a heart, the removal device 1500. As described above, the removal device can be delivered to the chamber of the heart using any suitable technique. For purpose of example and as embodied herein, the valve clip can be pre-positioned on a mitral valve leaflet, and the removal device can be delivered to a left ventricle of the heart beneath the mitral valve and the pre-positioned valve clip. The removal device 1500 includes a delivery catheter 1502, a grasping tool 1504, and a removal tool 1506 as described above.

The method further includes deploying the grasping tool 1504 to grasp a first portion 1508*a* of the valve clip 1508. The grasping tool 1504 can be deployed from the distal end portion 1502*a* of the delivery catheter 1502. As described above, the grasping tool 1504 can have any suitable configuration. For example, the grasping tool 1504 can include at least one hook 1516, and deploying the grasping tool 1504 can include grasping the first portion 1508*a* of the valve clip 1508 with the at least one hook 1516. Additionally or alternatively and as embodied herein, deploying the grasping tool 1504 can include moving the grasping tool 1504 from the open state 1504*a* to the closed state 1504*b*. For purpose of example and as embodied herein, the grasping tool 1504 can include opposing hooks 1516 coupled to move between the open state 1504*a* with distal ends 1516*a* of the opposing hooks 1516 spaced apart and the closed state 1504*b* with the distal ends 1516*a* of the opposing hooks 1516 adjacent each other. As embodied herein, deploying the grasping tool 1504 can include grasping the first portion 1508*a* of the valve clip 1508 between the distal ends 1516*a* of the opposing hooks 1516 in the closed state 1504*b*. With reference to FIG. 15B, the exemplary device 1500 is depicted with the grasping tool 1504 in an open state 1504*a*. As embodied herein, the opposing hooks 1516 of the grasping tool 1504 can extend from the distal 1502*a* end of the delivery catheter 1502 with the grasping tool 1504 in the open state 1504*a* and the opposing hooks 1516 can be positioned on opposing sides of the first portion 1508*a* of the valve clip 1508. FIG. 15C depicts the exemplary device 1500 with the grasping tool 1504 in a closed state 1504*b* and with the first portion 1508*a* of the valve clip 1508 grasped between the distal ends 1516*a* of the opposing hooks 1516 of the grasping device 1504. As described above, the grasping tool 1504 can be deployed using any suitable technique. For purpose of example and as embodied herein the grasping tool can be deployed by means of a spring bias. For example, retracting the delivery catheter 1502 relative to the grasping tool 1504 can cause the opposing hooks 1516 to spring open; advancing the delivery catheter 1502 relative to the grasping tool 1504 can cause the opposing hooks 1516 to be urged closed.

The method further includes manipulating the valve clip from an implanted condition to an elongated condition wherein the valve clip in the elongated condition has an elongated width less than an implanted width of the valve clip in the implanted condition. The grasping tool 1504 can manipulate the valve clip 1508 by grasping a first, distal end 1508*a* of the valve clip 1508 and applying a force in a distal direction. For example, manipulating the valve clip can include moving the grasping tool 1504 from the open state 1504*a* to the closed state 1504*b* and moving the grasping tool 1504 in a proximal direction. In doing so, the applied force can cause the valve clip 1508 to transition from the implanted condition to the elongated condition.

As explained above, removing the valve clip 1508 can include at least partially surrounding the valve clip 1508 with the removal tool 1506 when the valve clip 1508 is in the elongated condition. The removal tool 1506 can include a sheath 1520 defining a sheath lumen 1520*a* and at least partially surrounding the valve clip 1508 can include positioning the sheath to at least partially surround the valve clip 1508 within the sheath lumen. Removing the valve clip 1508 from the heart valve leaflet can include resecting the heart valve leaflet using a cutting blade. Additionally or alternatively, and as embodied herein, removing the valve clip 1508 from the heart valve leaflet 1510 can include ablating the heart valve leaflet 1510.

Another exemplary method in accordance with an aspect of the disclosed subject matter is described with reference to the exemplary device depicted in FIGS. 16A-E. Methods for removing a valve clip pre-positioned on a heart valve leaflet include delivering, to a chamber of a patient's heart, a removal device including a delivery catheter, a grasping tool, and a removal tool. The removal device can include any of the features described herein. Methods for removing a valve clip pre-positioned on a heart valve leaflet further include deploying the grasping tool from the delivery catheter to grasp the valve clip and manipulating the valve clip from an implanted condition to an elongated condition. As described above, the valve clip in the elongated condition has an elongated width less than an implanted width of the valve clip in the implanted condition. Methods for removing a valve clip pre-positioned on a heart valve leaflet further include at least partially surrounding the valve clip in the elongated condition with the removal tool, and removing the valve clip from the heart valve leaflet using the removal tool. The grasping tool 1604 can include a snare 1618, as described above. As embodied herein, deploying the grasping tool 1604 can include moving the grasping tool 1604 from the open state 1604*a* which defines a first diameter, to the closed state 1604*b* which defines a second, smaller diameter, can include grasping the first portion 1608*a* of the valve clip 1608 within the smaller, second diameter of the snare loop opening.

Another exemplary method in accordance with an aspect of the disclosed subject matter is described with reference to the exemplary device depicted in FIGS. 17A-D. Methods for removing a valve clip pre-positioned on a heart valve leaflet include delivering, to a chamber of a patient's heart, a removal device including a delivery catheter, a grasping tool, and a removal tool. The removal device can include any of the features described herein. Methods for removing a valve clip pre-positioned on a heart valve leaflet further include deploying the grasping tool from the delivery catheter to grasp the valve clip and manipulating the valve clip from an implanted condition to an elongated condition. As described above, the valve clip in the elongated condition has an elongated width less than an implanted width of the valve clip in the implanted condition. Methods for removing a valve clip pre-positioned on a heart valve leaflet further include at least partially surrounding the valve clip in the elongated condition with the removal tool, and removing the valve clip from the heart valve leaflet using the removal tool. As explained above, the grasping tool 1704 can include an alignment wire 1712. Deploying the grasping tool 1704 can therefore further include positioning the alignment wire 1712 within the loop opening of the snare 1718 to align the snare 1718 relative to the valve clip 1708.

Another exemplary method in accordance with an aspect of the disclosed subject matter is described with reference to the exemplary device depicted in FIGS. 18A-D. Methods for removing a valve clip pre-positioned on a heart valve leaflet include delivering, to a chamber of a patient's heart, a removal device including a delivery catheter, a grasping tool, and a removal tool. The removal device can include any of the features described herein. Methods for removing a valve clip pre-positioned on a heart valve leaflet further include deploying the grasping tool from the delivery catheter to grasp the valve clip and manipulating the valve clip from an implanted condition to an elongated condition. As described above, the valve clip in the elongated condition has an elongated width less than an implanted width of the valve clip in the implanted condition. Methods for removing a valve clip pre-positioned on a heart valve leaflet further include at least partially surrounding the valve clip in the elongated condition with the removal tool, and removing the valve clip from the heart valve leaflet using the removal tool. As embodied herein, the removal device 1800 can also include a stabilizing tool 1814. Manipulating the valve clip 1808 can include holding the second portion 1808*b* of the valve clip 1808 with stabilizing tool 1814 while the grasping tool 1804 grasps the first portion 1808*a* of the valve clip 1808. Further in accordance with the disclosed subject matter, the stabilizing tool 1814 can apply a second force to the valve clip 1808, wherein the second force is opposite the force applied to the valve clip 1808 by the grasping tool 1804.

All components listed herein may be made from any conventional medical device materials, such as stainless steel, nitinol, cobalt chrome, titanium, polyetheretherketone (PEEK), polyether block amide (PEBAX), ceramic, poly-L-lactic acid (PLLA), poly lactic-co-glycolic acid (PLGA), or other similar materials In some cases, it may be necessary to remove valve clips from a patient's heart after it has been installed and pre-positioned. Therefore, the valve clip can be manipulated before removal to prevent trauma to the patient. For example, the valve clip is depicted in FIG. 14A in an implanted condition 1400*a* (i.e., gripping the heart valve leaflets between respective gripping elements and fixation elements) currently require the use of large-bore removal catheters that can increase the risk of causing bleeding and/or healing issues in patients. In some such valve clips having large cross-sectional profiles, it may be necessary and possible to decrease the width of the cross-section by elongating the valve clip; for example and as depicted in FIG. 14B, this can be achieved by manipulating the valve clip from the wider, implanted condition 1400*a* to a nar-rower, elongated condition 1400*b*. In particular, the valve clip can be manipulated to the elongated condition 1400*b* by grasping and pulling on the distal portion of the valve clip 1408, thereby causing the respective gripping elements and fixation elements of the valve clip to invert and elongate. At this stage, due to leaflet tissue growth over one or both of the gripping elements and the fixation elements, it may be necessary to remove the heart valve tissue surrounding valve clip before removal. Preferably, a method described herein is performed as near the time that the valve clip is implanted as possible. In cases where heart valve tissue has more fully overgrown and fused the device to the heart valve leaflets, and/or in cases where heart valve tissue has fully bridged across the device, elongating the valve clip and cutting it from the valve leaflet tissue may not be possible; this stage is usually reached approximately one year after implantation of the valve clip. Therefore, the method described herein is most safely performed less than six months after implanta-tion, and preferably less than three months after implanta-tion.

Throughout this specification, plural instances may imple-ment components, operations, or structures described as a single instance. Although individual operations of one or more methods are illustrated and described as separate operations, one or more of the individual operations may be performed concurrently, and nothing requires that the opera-tions be performed in the order illustrated. Structures and functionality presented as separate components in example configurations may be implemented as a combined structure or component. Similarly, structures and functionality pre-sented as a single component may be implemented as separate components. These and other variations, modifica-tions, additions, and improvements fall within the scope of the subject matter herein.

Additionally, certain arrangements are described herein as including logic or a number of routines, subroutines, appli-cations, or instructions. These may constitute either software (e.g., code embodied on a non-transitory, machine-readable medium) or hardware. In hardware, the routines, etc., are tangible units capable of performing certain operations and may be configured or arranged in a certain manner. In example arrangements, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various arrangements, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to per-form certain operations. A hardware module may also com-prise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in tem-porarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering arrangements in which hard-ware modules are temporarily configured (e.g., pro-grammed), each of the hardware modules need not be configured or instantiated at any one instance in time. For example, where the hardware modules comprise a general-purpose processor configured using software, the general-purpose processor may be configured as respective different hardware modules at different times. Software may accord-ingly configure a processor, for example, to constitute a particular hardware module at one instance of time and to constitute a different hardware module at a different instance of time.

Hardware modules can provide information to, and receive information from, other hardware modules. Accord-ingly, the described hardware modules may be regarded as being communicatively coupled. Where multiple of such hardware modules exist contemporaneously, communica-tions may be achieved through signal transmission (e.g., over appropriate circuits and buses) that connect the hard-ware modules. In arrangements in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communi-catively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by soft-ware) or permanently configured to perform the relevant operations. Whether temporarily or permanently configured, such processors may constitute processor-implemented modules that operate to perform one or more operations or functions. The modules referred to herein may, in some example arrangements, comprise processor-implemented modules.

Similarly, the methods or routines described herein may be at least partially processor-implemented. For example, at least some of the operations of a method may be performed by one or more processors or processor-implemented hard-ware modules. The performance of certain of the operations may be distributed among the one or more processors, not only residing within a single machine, but deployed across a number of machines. In some example arrangements, the processor or processors may be located in a single location (e.g., within a home environment, an office environment or as a server farm), while in other arrangements the processors may be distributed across a number of locations.

The performance of certain of the operations may be distributed among the one or more processors, not only residing within a single machine, but deployed across a number of machines. In some example arrangements, the one or more processors or processor-implemented modules may be located in a single geographic location (e.g., within a home environment, an office environment, or a server farm). In other example arrangements, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

Some arrangements may be described using the expression "coupled" and "connected" along with their derivatives. For example, some arrangements may be described using the term "coupled" to indicate that two or more elements are in direct physical or electrical contact. The term "coupled," however, may also mean that two or more elements are not in direct contact with each other, but yet still co-operate or interact with each other. The arrangements are not limited This detailed description is to be construed as examples and does not describe every possible arrangement, as describing every possible arrangement would be impractical, if not impossible. One could implement numerous alternate arrangements, using either current technology or technology developed after the filing date of this application.

As used herein any reference to "one arrangement" or "an arrangement" means that a particular element, feature, structure, or characteristic described in connection with the arrangement is included in at least one arrangement. The appearances of the phrase "in one arrangement" in various places in the specification are not necessarily all referring to the same arrangement.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the arrangements herein. This is done merely for convenience and to give a general sense of the description. This description, and the claims that follow, should be read to include one or at least one and the singular also includes the plural unless it is obvious that it is meant otherwise.

While the present invention has been described with reference to specific examples, which are intended to be illustrative only and not to be limiting of the invention, it will be apparent to those of ordinary skill in the art that changes, additions and/or deletions may be made to the disclosed arrangements without departing from the spirit and scope of the invention.

The foregoing description is given for clearness of understanding; and no unnecessary limitations should be understood therefrom, as modifications within the scope of the invention may be apparent to those having ordinary skill in the art.

The invention claimed is:

1. A method of removing a valve clip pre-positioned on a heart valve leaflet comprising:

delivering, to a chamber of a heart, a removal device, the removal device comprising:

a delivery catheter having a distal end portion configured to be positioned near a heart valve;

a grasping tool deployable from the distal end portion of the delivery catheter, the grasping tool configured to grasp and manipulate a valve clip pre-positioned on a heart valve leaflet; and a removal tool extendable relative to the distal end portion of the delivery catheter, the removal tool configured to at least partially surround the valve clip and to remove the valve clip from the heart valve leaflet;

deploying the grasping tool to grasp a first portion of the valve clip;

manipulating the valve clip from an implanted condition to an elongated condition, wherein the valve clip in the elongated condition has an elongated width less than an implanted width of the valve clip in the implanted condition;

at least partially surrounding the valve clip in the elongated condition with the removal tool; and removing the valve clip from the heart valve leaflet using the removal tool.

2. The method of claim 1, wherein the grasping tool includes at least one hook, and wherein deploying the grasping tool includes grasping the first portion of the valve clip with the at least one hook.

3. The method of claim 1, wherein the grasping tool is configured to be moveable between an open state and a closed state, and wherein deploying the grasping tool comprises moving the grasping tool from the open state to the closed state.

4. The method of claim 3, wherein the grasping tool includes opposing hooks coupled to move between the open state with distal ends of the opposing hooks spaced apart and the closed state with the distal ends of the opposing hooks adjacent each other, and wherein deploying the grasping tool includes grasping the first portion of the valve clip between the distal ends of the opposing hooks in the closed state.

5. The method of claim 1, wherein the grasping tool includes a snare defining a loop opening configured to be moved from the open state with the loop opening defining a first diameter toward the closed state with the loop opening defining a smaller second diameter, and wherein deploying the grasping tool further comprises moving the snare from the open state to the closed state to grasp the first portion of the valve clip.

6. The method of claim 5, wherein the grasping tool further includes an alignment wire, and wherein deploying the grasping tool further comprises positioning the alignment wire within the loop opening of the snare to align the snare relative to the valve clip.

7. The method of claim 1, wherein the removal device further comprises a stabilizing tool configured to hold a second portion of the valve clip, and manipulating the valve clip further comprises holding the second portion of the valve clip with the stabilizing tool while the grasping tool grasps the first portion of the valve clip.

8. The method of claim 7, wherein the second portion of the valve clip is opposite the first portion of the valve clip.

9. The method of claim 7, wherein manipulating the valve clip includes applying a first force to the first portion of the valve clip with the grasping tool and applying a second force to the second portion of the valve clip with the stabilizing tool, the second force being opposite the first force.

10. The method of claim 7, wherein the first portion of the valve clip is a ventricular portion, and the second portion of the valve clip is an atrial portion.

11. The method of claim 1, wherein the removal tool comprises a sheath defining a sheath lumen, and wherein at least partially surrounding the valve clip includes positioning the sheath to at least partially surround the valve clip within the sheath lumen.

12. The method of claim 11, wherein the elongated width of the valve clip is less than an inner diameter of the sheath lumen.

13. The method of claim 1, wherein the removal tool comprises a cutting blade at a distal end of the sheath, and wherein removing the valve clip from the heart valve leaflet includes resecting the heart valve leaflet using the cutting blade.

14. The method of claim 1, wherein the removal tool comprises an ablation device, and removing the valve clip from the heart valve leaflet includes ablating the heart valve leaflet.

15. A method of removing a valve clip pre-positioned on a leaflet of a heart valve of a heart comprising:
    guiding a delivery catheter to the heart valve;
    grasping the valve clip with a grasping tool extending from the delivery catheter;
    manipulating the valve clip from a first condition in which the valve clip has a first width and a second condition in which the valve clip has a second width less than the first width;
    positioning a sheath at least partially about the valve clip while being grasped by the grasping tool; and
    removing the valve clip from the heart.

16. The method of claim 15, further comprising resecting the valve clip from the valve leaflet using a removal tool.

17. The method of claim 16, wherein the removal tool includes one of a blade and an ablation device, and the resecting step includes one of cutting the leaflet and ablating the leaflet.

18. The method of claim 15, wherein, in the first condition, the valve clip has a first length, and in the second condition, the valve clip has a second length greater than the first length, the first and second lengths each extending perpendicular to the first and second widths, respectively.

19. The method of claim 15, wherein the grasping tool includes a snare, and the grasping step includes moving the grasping tool from a first state in which the snare defines a first diameter and a second state in which the snare defines a second diameter smaller than the first diameter.

20. The method of claim 15, wherein the grasping tool includes a first member and a second member, and the grasping step includes positioning a portion of the valve clip between the first and second members while in an open configuration, and moving the first and second members toward a closed configuration to engage the valve clip with the first and second members.

21. The method of claim 15, further comprising retracting the implant within the delivery catheter while in the extended position.

22. The method of claim 15, wherein the heart valve is a mitral valve, and the guiding step includes transapically passing the delivery catheter into the left ventricle.

23. The method of claim 15, wherein a first portion of the valve clip is positioned within an atrium of the heart and a second portion of the valve clip is positioned within a ventricle of the heart, and the grasping step includes grasping the first portion of the valve clip with the grasping tool.

24. The method of claim 23, further comprising engaging the second portion of the valve clip with a stabilizing tool, and the manipulating step includes applying a first force on the first portion with the grasping tool and a second force on the second portion with the stabilizing tool, the second force opposing the first force.

25. The method of claim 15, wherein, in the first condition, a portion of the valve clip is folded over onto itself to grasp the leaflet therebetween, and in the second condition, the portion of the valve clip is unfolded.

\* \* \* \* \*